United States Patent
Vega et al.

(10) Patent No.: US 11,972,277 B2
(45) Date of Patent: Apr. 30, 2024

(54) EMOTIONALLY DRIVEN SOFTWARE INTERACTION EXPERIENCE

(71) Applicant: LOVINGLY, LLC, Fishkill, NY (US)

(72) Inventors: Joseph Vega, Hopewell Junction, NY (US); Kenny Garland, Hopewell Junction, NY (US); Daniela Virginia Marquez, Poughkeepsie, NY (US); Marque Nolan Staneluis, Bronx, NY (US); Dennis Park-Rodriguez, Hopewell Junction, NY (US); Ryan Wesley A. Lowe, Cold Spring, NY (US); Lakshmi Pillai, Fishkill, NY (US); James Craig Rosenthal, Newburgh, NY (US); Matthew Zangen, New Paltz, NY (US); Kaitlin Heather Schupp, Kingston, NY (US); Danielle Sarah Gorton, Beacon, NY (US)

(73) Assignee: LOVINGLY, LLC, Fishkill, NY (US)

( * ) Notice: Subject to any disclaimer, the term of this patent is extended or adjusted under 35 U.S.C. 154(b) by 0 days.

(21) Appl. No.: 16/874,987

(22) Filed: May 15, 2020

(65) Prior Publication Data
US 2020/0364068 A1   Nov. 19, 2020

Related U.S. Application Data

(60) Provisional application No. 62/968,547, filed on Jan. 31, 2020, provisional application No. 62/848,634, filed on May 16, 2019.

(51) Int. Cl.
*G06F 9/451* (2018.01)
*G06F 3/0482* (2013.01)
(Continued)

(52) U.S. Cl.
CPC .......... *G06F 9/453* (2018.02); *G06F 3/0482* (2013.01); *G06F 9/542* (2013.01);
(Continued)

(58) Field of Classification Search
CPC ...... G06F 16/436; G06F 9/453; G06F 3/0482; G06F 9/542; G06F 19/348; G06F 40/35;
(Continued)

(56) References Cited

U.S. PATENT DOCUMENTS

| 7,720,784 B1 * | 5/2010 | Froloff | G06F 40/20 706/47 |
| 9,009,096 B2 | 4/2015 | Pinckney et al. | |

(Continued)

FOREIGN PATENT DOCUMENTS

WO    2010128347 A1    11/2010

OTHER PUBLICATIONS

Dibitonto et al., "Chatbot in a Campus Environment: Design of LISA, a Virtual Assistant to Help Students in Their University Life". In: Kurosu, M. (eds) Human-Computer Interaction. Interaction Technologies. HCI 2018. https://doi.org/10.1007/978-3-319-91250-9_9, pp. 103-116 (Year: 2018).*

(Continued)

*Primary Examiner* — Andrew L Tank
(74) *Attorney, Agent, or Firm* — Tono Law Group, LLC; Karen Tonoyan

(57) ABSTRACT

A method for ascertaining an emotional goal includes receiving, via an emotionally responsive computerized system having a user interface communicatively coupled to a networked user device including a processor device, user-input concerning a purpose of a user's interaction with a software interface. It can include registering input indicating a target person to whom the purpose of the user's interaction pertains and prompting the user to provide a root motivator (Continued)

comprising a root emotion or a root reason for the interaction. Some variations include generating a user-perceptible output and a set of user interface elements dependent on the root motivator along with obtaining the user's specific emotional goal with respect to the target person on the basis of user-inputs in response to a presentation of a sequence of user interface elements, to provide the user, via the software interface, a recommendation regarding a fulfillment of the specific emotional goal.

20 Claims, 13 Drawing Sheets

(51) Int. Cl.
    *G06F 9/54*         (2006.01)
    *G06F 16/2457*     (2019.01)
    *G06F 16/435*      (2019.01)
    *G06F 16/9535*     (2019.01)
    *G06F 40/35*       (2020.01)
    *A61B 5/16*        (2006.01)

(52) U.S. Cl.
    CPC ........ *G06F 16/2457* (2019.01); *G06F 16/436* (2019.01); *G06F 16/9535* (2019.01); *G06F 40/35* (2020.01); *A61B 5/165* (2013.01)

(58) Field of Classification Search
    CPC . G06F 16/2457; G06F 16/9535; G16H 20/70; G16H 50/20; G10L 25/63; A61B 5/165; A61B 5/167; A61M 2205/502; G06Q 30/0251; G06Q 30/0257; G06Q 30/0271; G06Q 30/0631; G06Q 30/0643
    See application file for complete search history.

(56) References Cited

U.S. PATENT DOCUMENTS

| | | | |
|---|---|---|---|
| 9,171,048 B2* | 10/2015 | Brust | G06F 3/0481 |
| 9,318,108 B2 | 4/2016 | Gruber et al. | |
| 9,875,483 B2 | 1/2018 | Stoll et al. | |
| 9,996,531 B1 | 6/2018 | Parastatidis et al. | |
| 10,049,663 B2 | 8/2018 | Orr et al. | |
| 10,185,983 B2 | 1/2019 | Guo et al. | |
| 10,348,658 B2 | 7/2019 | Rodriguez et al. | |
| 10,740,568 B2* | 8/2020 | Azmoon | G06F 3/0481 |
| 2009/0234755 A1* | 9/2009 | Sidoruk | G06Q 30/0603 705/26.1 |
| 2010/0312547 A1 | 12/2010 | Van Os et al. | |
| 2011/0183305 A1* | 7/2011 | Orbach | A61B 5/16 434/236 |
| 2011/0252348 A1 | 10/2011 | Fingerer et al. | |
| 2011/0302117 A1* | 12/2011 | Pinckney | G06N 20/00 706/12 |
| 2012/0117005 A1* | 5/2012 | Spivack | G06F 16/3329 706/11 |
| 2012/0245987 A1 | 9/2012 | Isaacson et al. | |
| 2013/0332308 A1 | 12/2013 | Linden et al. | |
| 2014/0039975 A1* | 2/2014 | Hill | A61B 5/167 705/7.29 |
| 2014/0052563 A1 | 2/2014 | Watkins et al. | |
| 2014/0223462 A1* | 8/2014 | Aimone | A61B 5/369 725/10 |
| 2014/0276244 A1* | 9/2014 | Kamyar | A61B 5/7435 600/595 |
| 2014/0351332 A1* | 11/2014 | Ben-Kiki | H04L 51/32 709/204 |
| 2014/0379615 A1 | 12/2014 | Brigham et al. | |
| 2015/0154684 A1* | 6/2015 | Korobkov | G06Q 30/0631 705/14.66 |
| 2016/0171598 A1 | 6/2016 | Rice et al. | |
| 2016/0203729 A1* | 7/2016 | Zilca | G16H 50/20 434/236 |
| 2016/0232131 A1* | 8/2016 | Liu | G06F 40/103 |
| 2016/0275584 A1* | 9/2016 | Gibson | G06Q 30/0621 |
| 2017/0140563 A1* | 5/2017 | No | H04N 1/00198 |
| 2017/0250930 A1 | 8/2017 | Ben-Itzhak | |
| 2017/0262604 A1* | 9/2017 | Francois | G16H 50/20 |
| 2018/0113583 A1 | 4/2018 | Jain et al. | |
| 2018/0229372 A1* | 8/2018 | Breazeal | B25J 11/001 |
| 2020/0110519 A1 | 4/2020 | Vangala et al. | |
| 2020/0159724 A1* | 5/2020 | Nguyen | G06F 16/9035 |

OTHER PUBLICATIONS

Huang, Ting-Hao, Kenneth, et al., "" Is There Anything Else I Can Help You With?" Challenges in Deploying an On-Demand Crowd-Powered Conversational Agent." Fourth AAAI Conference on Human Computation and Crowdsourcing, Sep. 2016, pp. 79-88.

Kandhari, Mandeep Singh, et al., "A Voice Controlled E-Commerce Web Application." 2018 IEEE 9th Annual Information Technology, Electronics and Mobile Communication Conference (IEMCON). IEEE, Nov. 2018, 7 pages.

Chai, Joyce, et al., "Natural language assistant: A dialog system for online product recommendation." AI Magazine, Jun. 2002, pp. 63-76, 23.3.

McRoberts, Sarah, et al., "Exploring Interactions with Voice-Controlled TV." arXiv preprint arXiv, May 2019, pp. 1-11, 1905. 05851.

Sun, Yueming, et al., "Conversational recommender system." The 41st International ACM SIGIR Conference on Research & Development in Information Retrieval, Jun. 2018, pp. 235-244.

Qu, Chen, et al., "Analyzing and characterizing user intent in information-seeking conversations." The 41st International ACM SIGIR Conference on Research & Development in Information Retrieval, Jun. 2018, pp. 989-992.

Christakopoulou, Konstantina, et al., "Towards conversational recommender systems." Proceedings of the 22nd ACM SIGKDD international conference on knowledge discovery and data mining, Aug. 2016, pp. 815-824.

"Add deep logic (expertise) to your AI support assistant," https://exvisory.ai, Sep. 6, 2019, 5 pages.

Morgan, "10 Customer Experience Implementations of Artificial Intelligence" (2018) Forbes.com, Feb. 8, 2018, 5 pages.

Heussner, "Gifting 2.0: Letting the Web Pick Presents for Your Friends" ABCNews.com, Nov. 29, 2010, 5 pages.

Gault, "How Customization is the 'Glass Slipper' Solution For E-commerce Evolution" Forbes.com (Year: 2018).

* cited by examiner

EMOTIONALLY DRIVEN SOFTWARE INTERACTION EXPERIENCE

This application claims priority to U.S. Provisional Application No. 62/848,634, filed on May 16, 2019, and U.S. Provisional Application No. 62/968,547, filed on Jan. 31, 2020, each of which is incorporated herein by reference in its entirety.

BACKGROUND

The present invention generally relates to providing a dynamically interactive software experience to a user that is dependent on an emotional state or intention. More particularly, the invention relates to ascertaining a user emotional goal to provide the user recommendations regarding the fulfillment of that goal through a customized and dynamic software experience.

Conventional software interaction experiences, including those pertaining to e-commerce, corporate productivity, service-provision, and the like, are commonly presented as static web or application interfaces that don't change, respond, or assist a user with respect to an emotional state or intention that they may have. For example, conventional interactions on websites, applications, and other software services generally remain the same regardless of the mood or emotional state of the user. This state of affairs becomes problematic for users who seek to have their interaction with software interfaces reflect their emotional states or goals because the static framework of conventional interaction often poorly corresponds to the purposes of the interaction with the software and the fulfillment of the emotional goals that the users may have.

Accordingly, for the foregoing reasons, there is a need for a system and method for ascertaining a user's emotional goal with a high level of precision and providing recommendations aimed at the fulfillment of that goal. Likewise, there is a need for a system and method providing a dynamic interactive software experience which is reflective of a user's emotional state and intentions.

SUMMARY

Embodiments of the present invention are directed to systems and methods that ascertain an emotional goal and can therefore provide specific recommendations directed towards achieving that goal. The embodiments can further provide a dynamic and interactive user interaction experience that is consistent with an identified emotion.

In accordance with an embodiment of the present invention, a computer implemented method for ascertaining an emotional goal includes receiving, via an emotionally responsive computerized system having a user interface communicatively coupled to a networked user device including a processor device, a first user-input concerning a purpose of a user's interaction with a software interface. It can further include registering a second user-input indicative of a target person to whom the purpose of the user's interaction pertains and prompting the user to provide at least one root motivator comprising a root emotion or a root reason for the interaction. Some variations of the invention also include generating a user-perceptible output and a set of user interface elements dependent on at least one root motivator along with obtaining the user's specific emotional goal with respect to the target person on the basis of user-inputs in response to a presentation of a sequence of user interface elements to provide the user via the software interface a recommendation regarding a fulfillment of the specific emotional goal. In some cases, generating the user-perceptible output and the set of user interface elements includes the output being and elements in the set of user interface generating images or sounds that are semantically, tonally, thematically, or chromatically related to at least one root motivator. The generation of a subsequent user interface element and the generation of a subsequent output can respectively be dependent, at least in part, on a preceding user interface element interaction and each subsequent user interface element in the sequence presented to the user that includes a prompt or query can elicit a more precise description of the user's emotional goal with higher specificity than the description elicited by a preceding prompt or query. In some versions of the invention, the user interface and its elements, as well as outputs presented to a user, can be visually displayed on a screen coupled to a touch sensitive input means that the user can use to interact with embodiments of the invention. Alternatively, a user interface device through which user interface elements and outputs can be presented to a user can be an audio input-output device configured to emit sounds and receive voice input.

In accordance with an embodiment of the present invention, a non-transitory computer readable medium includes instructions that are executable by a computing device which when executed can cause the computing device to register a first user-input concerning a purpose of a user's interaction with a software interface of the computing device as well as a second user-input indicative of a target person to whom the purpose of the user's interaction pertains. The instructions can also cause the computing device to prompt the user to provide one or more root motivators, including a root emotion or a root reason, for the interaction and then generate a user-perceptible output and a set of user interface elements dependent on at least one root motivator. Some versions of the invention have instructions that can then obtain the user's specific emotional goal with respect to the target person on the basis of the user's inputs in response to the presentation of a sequence of user interface elements, and that can also provide the user, via the software interface, a recommendation regarding a fulfillment of the specific emotional goal. In some instances, the user-perceptible output and elements in the set of user interface elements can be reflective of a theme consistent with at least one root motivator and can have the user-perceptible output and/or the user interface elements include images or sounds that are semantically, tonally, thematically, or chromatically related to at least one root motivator. Some versions of the invention can have each of a subsequent user interface element and a subsequent output be respectively dependent on a preceding user interface element interaction. In some cases, the elements of the set of user interface elements can be presented to a user in a sequence wherein each subsequent user interface element includes a prompt or query eliciting a more precise description of the user's emotional goal than that provided by the user in response to a previous prompt or query presented to the user earlier in the sequence. Further, the instructions can also cause the computing device to present the user-perceptible output and interface elements to a user via a screen, an audio input-output device, or both the screen and the audio input-output device.

In accordance with an embodiment, the system for ascertaining an emotional goal includes at least one computing device that has at least one processor device and at least one user interface including an input means and output means communicatively connected to the processor. The system can also have the computing device receive a first user-input, via the at least one user interface, that is indicative of a purpose of a user's interaction with the at least one user interface as well as a second user-input indicative of a target person (which could be the user themselves) to whom the purpose of the user's interaction pertains. In some cases, the computing device of the system can, by using the processor device, generate a prompt in response to the first and second user-input for the user to provide at least one root motivator that can include a root emotion or a root reason for the interaction. The computing device can also generate user-perceptible output and a set of user interface elements dependent on at least one root motivator and present the output and the set of elements to the user via the output means. In some embodiments of the invention, the computer device can determine the user's specific emotional goal with respect to the target person on the basis of the user-inputs in response to a presentation of a sequence of user interface elements and can also provide, via the output means, for the user a recommendation regarding a fulfillment of the specific emotional goal. In some cases, the user-perceptible output and elements in the set of user interface elements can be reflective of a theme consistent with at least one root motivator. In at least one version of the invention, subsequent user interface element and subsequent outputs can be respectively dependent on preceding user interface element interactions, and elements of the set of user interface elements can be presented to a user in a sequence where each subsequent user interface element includes a prompt or query eliciting a more precise description of the user's emotional goal than that provided by the user in response to a previous prompt or query presented to the user earlier in the sequence These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Figure 1:
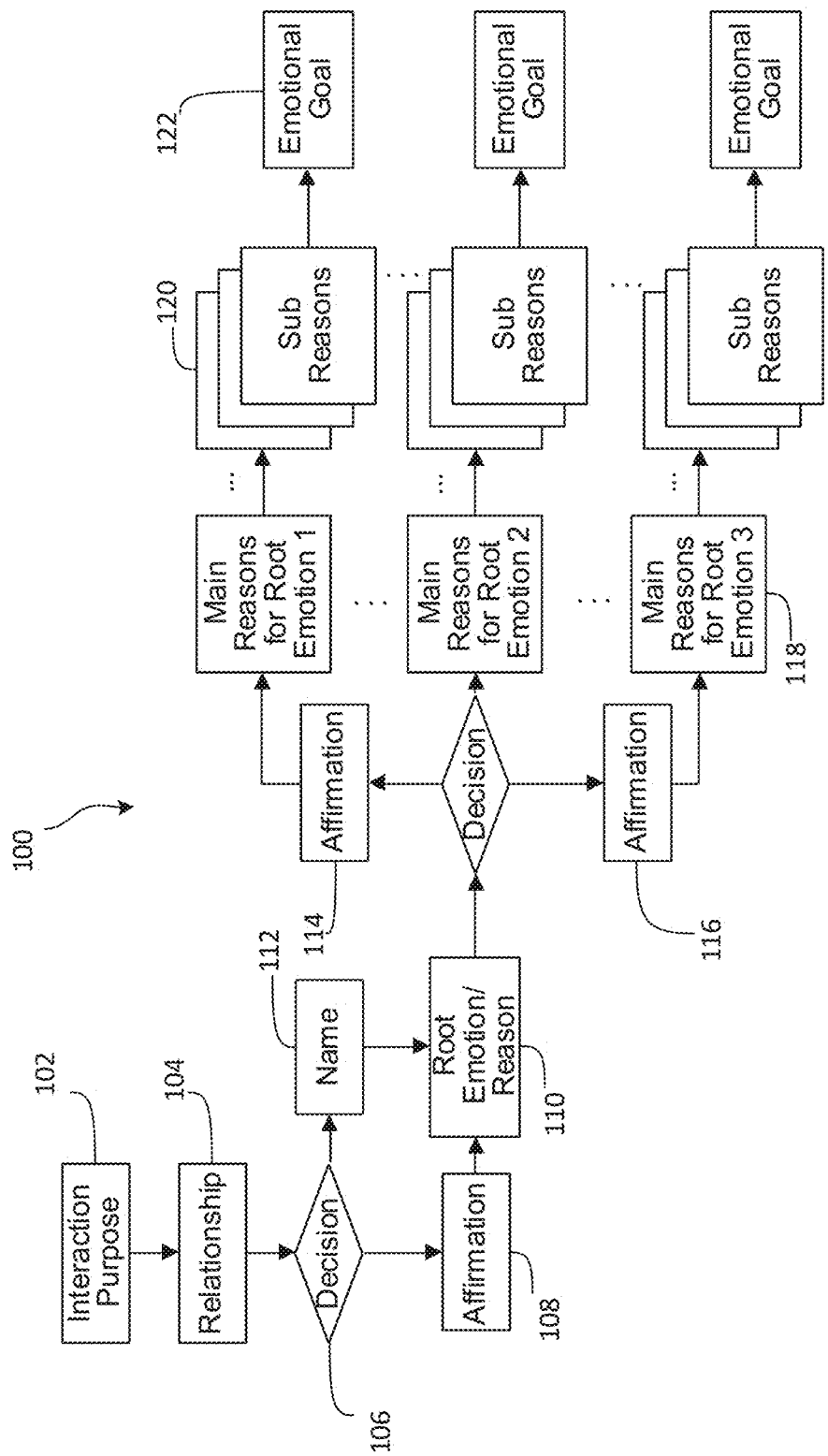
FIG. 1 is a flow chart of a method for ascertaining an emotional goal, in accordance with an embodiment of the present invention.

In the Summary above and in this Detailed Description, and the claims below, and in the accompanying drawings, reference is made to particular features of various embodiments of the invention. It is to be understood that the disclosure of the various versions of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

Embodiments of the invention relate to systems and methods of providing an emotion-driven software experience and identifying an emotional goal. Employment of the systems and methods described herein provides a user with an experience that dynamically changes and interacts with the user according to an emotion experienced by or indicated by a user, determines a specific emotional goal, and facilitates achievement of the emotional goal by providing a recommendation.

In general, embodiments of the invention incorporate the use of an interactive physical interface capable of presenting a dynamically responsive audio, video, or audio-video software interface through which questions and prompts as well as other output can be presented to a user. The same interactive interface or an alternative one can also be used to produce outputs perceivable by the user and to receive input and selections from the user, some of which may be entered by the user in response to the aforementioned questions and/or prompts.

An objective of the various systems and methods described herein is to ascertain or to assist in ascertaining a user's emotional goal. The function of the potential questions, prompts, and/or outputs that may be presented to a user is to narrow down, focus on, and identify, with increasing specificity, a user's desired or intended emotional goal so that a recommendation relating to the fulfillment of that emotional goal can then be made. Notably, the herein described systems and methods are flexible and include the option for a user to skip questions and/or prompts. Furthermore, it is readily contemplated that embodiments of the invention can include questions and/or prompts to be either automatically learned by the embodiment through user interaction or that can be added manually to the software interface through periodic updates of the embodiment.

Unlike conventional software interaction experiences, the various embodiments presented herein are dynamically responsive to a user's emotion or emotional intention. The several versions of the invention seek to provide changing software behavior based on an understanding or identification of a user's emotional (or psychological) state. Accordingly, one of the goals achieved thereby is the provision of a better, more natural, dynamic experience of interacting with the software (and its interface) and the humanization of that which conventionally would otherwise be a static transactional process. By making the interaction with the software dynamic and contingent on a user's emotion(s), the various embodiments emulate human interaction to the extent that they react and adjust aspects and characteristics of the interaction in accordance with the perceived emotional state or condition of the user. Notably, it is not just the outcome of the interaction that is dependent on the identified emotion, but rather the entirety of the interaction including its constituent steps or stages and their qualities that become contingent on and follow from the emotion as well.

Some versions of the invention operate in a manner dependent on the collection of userinputs such that the user's interaction with a software interface, the experience of that interaction including the perception of the user interface elements (e.g., questions, prompts, and selection options), and the manner in which they are presented, can be dynamic and responsive based on the emotional state and intent of the user. Subsequent actions, results (obtained at the conclusion of an interactive process), and outputs presented during the course of a user's interaction with a software interface of the invention can depend on the understanding (i.e., identifying/defining) a root emotional cause as well as supporting emotional details of that root cause (e.g., sub-emotions, reasons, sub-reasons, etc.) motivating the user to pursue an emotional goal and driving the user's interaction with the embodiment. If some information that was attempted or prompted to be collected in the course of a user's interaction with a software interface was not or could not be obtained through the completion of the several stages of a process in accordance with an embodiment of the invention, the embodiment is able to accommodate for the missing information with pre-determined default states for the selections, interaction options, interface element (e.g., prompt, questions, buttons, pictures, sounds, etc.) that can be substituted in lieu of user-input for the remaining stages of the user's interaction with the software interface. In this manner, the embodiment can be flexible enough to cater to highly varied circumstances and provide a custom emotion-driven experience is to the user regardless of how much or how little information is provided by the user.

It should be understood that although versions of the invention will be described herein primarily in the context of the floral industry and the gift-purchasing context, other embodiments of the invention are contemplated to be used more broadly in a variety of industries, including applications in the e-commerce (e.g., online sales), self-help, and service provision contexts and applicable industries. A person skilled in the art should find that the systems and methods for ascertaining an emotional goal, providing a suggestion for fulfilling that goal, and providing a dynamic software interaction experience can be applied in a variety of contexts and operating environments that may include software used for the purposes of self-help, psychotherapy, or dating.

The systems and methods described herein provide an emotion-driven software interaction experience that seeks to not only identify the emotional state or condition of the user and facilitate the conveyance of an emotion to a target individual (e.g., a recipient), but to also propagate that emotional state to be reflected in the various stages of the interaction. Conveyance of the desired emotion to the target individual can be realized in a variety of ways including, but not limited to, through the presentation of a gift, a card message, or multi-media content.

The descriptions provided below can include several recurring elements to aid in the understanding of the examples of the invention including elements referred to as prompts, affirmations, software interactions, and outputs. Prompts can be understood to be any manner of invitations or suggestions for a user to provide information and can include questions, open ended statements, fillable fields, and selection options. Affirmations can be understood to be automatically presented responses provided immediately after a particular user interaction with the software interface (e.g., answering questions, making selections via user interface elements, and responding to prompts) that dynamically reflect the sentiments and emotions that may have been indicated or implied by that interaction (e.g., an affirmation can include a "Yay Exciting!" statement in response to a "Celebrating Something" answer being provided by a user). Additionally, affirmations can contain the appropriate relevant tone and be presented in a manner that is thematically and logically consistent with emotional information gleaned from the user's interaction with the software interface. It should be understood that the phrase "software interface" may refer to any type of user interface with which a user can interact and includes any interactive elements that a user can engage or provide input through as well as any outputs produced as a result of such engagement. Accordingly, as used herein, the phrase "software interactions" include the interactions of a user with a software interface of a version of the invention and can include responses to questions or prompts, selections being made via user interface elements presented to the user, and input being provided by a user.

The logic followed in the presentation of prompts and/or questions to a user can follow a pattern where subsequent questions/prompts appearing during a user's interaction with the software interface depend on answers, responses, or input provided at an earlier time during the user's interaction so that a deeper emotional understanding of the user's intention can be ascertained. For example, after a user enters an answer to a question and receives the aforementioned affirmation, the dynamically contingent question of "What are you celebrating" may be asked to further clarify the user's emotional goal or intention. It should be noted that the arrangement, appearance, and perception of user interface elements presented to the user can be guided based on the reuse of emotional elements and answers presented or provided at an earlier point of the user's interaction with the software interface. Consequently, visual cues or elements (e.g., pictures, photographs, diagrams, etc.), color, imagery, textual elements including the choice of words and phrasing, as well as potential audio elements can be customized to be adapted to correspond to and blend with an emotion indicated or elicited from the user. Thus, the user interface elements can adapt based on an identified emotion (e.g., bright colors and cheery sounds can be used in situations where a celebratory emotion is indicated and reuse language that reinforces happiness and celebration throughout the course of a user's interaction with the software interface). However, as described in more detail below, a key element in the inventive processes described herein is the establishment or identification of a primary or root cause or root emotion that can set the mood and serve as a basis for tailoring the rest of the user's experience of interacting with the software interface. It is from this root emotional motivator that the remaining interactions stem in the various embodiments of the invention.

Referring now to the drawings in which like numerals represent the same or similar elements and initially to FIG. 1, an exemplary method for ascertaining an emotional goal and for providing a emotion-driven software interaction experience is provided. Initially, the purpose of a user's interaction 102 with the software via its interface may be indicated by a user. Exemplary purposes may include, but are not limited to, a gift purchase, a presentation of a floral arrangement, self-improvement, or dating, each of which can have a target individual (i.e., an individual who is intended to ultimately be the beneficiary of the result of the interaction). Once a purpose of interaction is indicated or selected by the user, the user may be prompted to indicate or select a relationship 104 between the user and the target individual. Notably, the target individual can be the same person as the user, especially in the case of a self-help or psychotherapy software application implementation of an embodiment of the invention (i.e., the user intend him/herself to be the intended ultimate beneficiary of the interaction).

After an input by a user is provided, a decision 106 can be made to provide an appropriate subsequent user interface element or output that logically stems from the input provided by the user. Subsequently, if a relationship 104 is indicated or selected, a user may be prompted to provide additional details about the relationship, such as, for example, the target individual's name 112. In some cases, after providing input, a user may be presented with an affirmation 108 which, as described above, can be a response that is logically related to that input. With the aforementioned information having been provided by the user, the user can then be prompted to indicate or select one or more root emotion 110 or root reason (each of "root emotion" and "root reason" also referred to herein as a 218) for the user's interaction with the software. This root emotion 110 or reason can then serve as the basis for the subsequent presentation of interface elements and outputs for user interaction as well as the basis for further, more specific, determination of the user's emotional goal.

As noted earlier, similar to times after other instances of user input being provided, subsequent to the user providing the root emotion 110 or root reason for the interaction, the user can be presented with an affirmation 114, 116 or other response that is logically or emotionally related to the root emotion 110 or root reason. This provision of a root emotion 110 or root reason can begin a process that may be referred to herein as an "emotional funnel" to the extent that the process is directed towards ascertaining the user's emotional goal with ever more precision and specificity at each subsequent stage of the process. Then, having provided the root emotion 110 or root reason, the user can be prompted to indicate or select a main reason 118 in support of the root emotion 110 or root reason, that further specifies the user's emotional intent from one that was conceptually broader to one that is conceptually narrower and more precise. Notably, it should be understood that the various embodiments of the invention contemplate the provision of any of a variety of root emotions 110 or reasons as well as any of a variety of applicable main reasons 118 logically stemming therefrom. Subsequently, the user can be provided with an affirmation (similar to ones described above) after having provided an input, or, the user can be prompted to provide a sub reason 120 for the main reason 118. The sub reason 120 provided by the user, can then serve to further specify and more precisely articulate the user's emotional intent. Accordingly, the process of iteratively affirming a user's previous input and/or prompting the user to provide more specific details regarding the user's emotional intent can be repeated an arbitrary number of times until the desired level of precision for the identification or determination of the user's emotional goal 122 is achieved. It should be understood that the level of depth or precision desired and, consequently, the number of iterative stages can be either decided by the user or pre-determined by a setting of the software. In this manner a precise determination of a user's emotional goal 122 can be made which can then serve as a basis for providing the user a recommendation for the fulfillment of that emotional goal 122.

The user interface interaction identifying the user's relationship 104 to the target individual can be employed to further characterize a user's emotional state or emotional intention, particularly in instances where an embodiment of the invention is operated in the context of gift-giving, and can also be a factor in determining a pre-determined set of root emotions 110 that a user may opt to choose from instead of providing one by free entry into a fillable field without selecting from a pre-determined set. It should be understood that throughout the course of a user's interaction with the software interface of an embodiment of the invention, a plurality of various user interface elements may be presented to the user, each of which may be dynamic and changeable with respect and in response to an input provided by the user. In this manner, dynamic elements can be leveraged or affected to provide a more natural interaction experience to the user that is thematically consistent with an input that the user provided. For example, because a key input that a user may provide is a root emotion 110 or reason, subsequent user interface elements or outputs of an embodiment can be adjusted to reflect or correspond with that root emotion 110 or reason.

As discussed in more detail below, images, sounds, and interactive elements presented to the user may be chosen or adjusted to correspond to an emotion by being semantically (i.e., in general meaning), tonally (e.g., by general overarching color tone or sound pitch/frequency), thematically (e.g., by belonging to a particular conceptual category), or chromatically (e.g., by the variety of the selection of colors used or primary note sound used) consistent therewith. Because of the importance given to identifying the relationship between the user and the target individual, the emotion-driven interactive software experience can inherit or adopt some aspects, qualities, or properties of the relationship to provide a more human-like and customized interaction to the user (e.g., in the context of an embodiment of the invention being used for gift-giving, the product name or message can include the relationship 104 or target individual's name 112 to make the gift more personal).

It should be understood that the initial purpose 102 of interacting with the software indicated by the user can determine the remainder of the emotionally-driven interactive software experience as that initial purpose 102 can define the realm of possibilities of why a user may be feeling physically, emotionally, or psychologically and provide basic information about why they chose to initiate the interaction with the software. Consequently, that information may determine the presence or availability of options or user interface elements appearing in subsequent stages of the users interaction with the software interface. On the basis of that purpose 102, in some embodiments, the user can be prompted to provide information that can help understand the deeper meaning or reason for the interaction so that the interaction can be customized to deliver a proper (i.e., appropriate, corresponding) emotional response through the use of imagery and tone applicable to the various user interface elements, and outputs provided to the user throughout the course of a user's experience of interacting with the embodiment of the invention. It should be noted that, as used herein, "tone" can refer to an aspect of a user interface element or an output that can be adjusted to correspond with a root emotion 110 or root reason provided by the user. For example, the number of times a user is prompted for input, the verbiage of the prompts, the color scheme, and the types of user interface elements presented can be varied in order to correspond semantically, tonally, thematically, or chromatically with a root emotion 110. Further, it should be also understood that the presentation of a recommendation (including a potential course of action, message, product, or service) for the fulfillment of a user's emotional goal 122 can likewise be semantically, tonally, thematically, or chromatically reflective of or corresponding with the root emotion 110 or reason.

An exemplary method for ascertaining a user's emotional goal may begin with the identification of a basic root emotion 110 or reason (e.g., "celebrating" or "thinking of you") that can then dictate or filter the subsequent, more specific, identification of a more precise emotional intention (e.g., "celebrating a birthday" or "expressing sympathy for a loss"). The visual and/or audio outputs (e.g., cues) and interface elements presented to a user can reflect or be sensitive to the root reason or emotion 110 provided, and thereby make the remainder of the software interaction experience be reflective and representative of that root emotion. Further, based on the root emotion 110 or root reason, subsequent prompts or questions can be presented to a user to further ascertain the user's emotional intent with more precision to a level of specificity that can be determined by the user (e.g., "celebrating because it's my aunt's $50^{th}$ golden birthday"). Accordingly, this more precise identification of a user's emotional intent, can itself further influence the customization and adaptation of the output and user interface elements selected to be presented to the user at subsequent stages of the interaction with the software interface. Thus, the interface elements and the interaction therewith can become contingent upon a previous input provided by the user as the audio and/or visual user interface elements and outputs (e.g., cues) are presented in correspondence with a user's identification of the user's emotion and reason.

In some instances, a user's emotional state and their emotional goal or emotional intention may not coincide with each other. In such cases, a user may want to convey an emotion to the target individual that is different from the one that they themselves are experiencing (e.g., the user is sad because their aunt passed away, but the user's emotional goal is to make the target individual, the user's cousin, feel loved and supported since the cousin's mother passed away). Accordingly, subsequent interaction with the software interface, defined by the user interface elements and outputs presented to the user, can be independent of or inconsistent with the user's emotional state, but instead rather be dependent on and consistent with the emotional goal or intent that the user has with respect to the target individual. By presenting the user with prompts to provide additional information that may pertain to the emotional goal that the user desires to achieve, the experience of interacting with the emotion-driven software can culminate in the recommendation of a product, service, or course of action that fulfills the user's emotional goal.

The various versions of the invention can be configured for use with different initial purposes of interaction, including, as mentioned earlier, purposes related to self-help, psychotherapy, and dating in addition to emotional message conveyance and gift-giving. For example, a user may desire to improve their social skills or abilities of interacting with others and choose to interact with an embodiment of the invention in order to better understand the user's own emotional state and emotional intentions. In such a scenario, through an iterative process of being prompted to provide more detailed emotional information and interacting with the user interface elements of an embodiment, the user can be presented with an articulation of their emotional state or emotional desire with a level of specificity that the user themselves may not have been able to achieve unaided. In embodiments of the invention in which affirmations are presented after user input is provided, such an exercise may also be used for the purposes of self-reflection and personal understanding that can improve a user's psychological well-being.

Further, it should be understood that user interaction as described herein can be realized through the use of various input and output means. For example, user-perceptible visual output can be provided to a user through the use of a screen connected to an input means. In such cases, a user can be presented with visual prompts (e.g., questions, fillable fields, menus, selection choices, etc.) to provide input (e.g., information regarding an emotional state or emotional goal) to a software interface. Alternatively, user-perceptible audio output can be provided to a user through an audio device such as a speaker. Accordingly, a user can be presented with audible questions or prompts to provide information as well as with options or choices from which a selection can be made. Similarly, user-input can be received using a tactile or a touch-sensitive device as well as through a device capable of registering sound. For example, a user may input responses to the prompts presented to the user using a computer peripheral (e.g., a mouse, keyboard), a touch-screen, a microphone, or a combination of such devices.

Figure 2A:
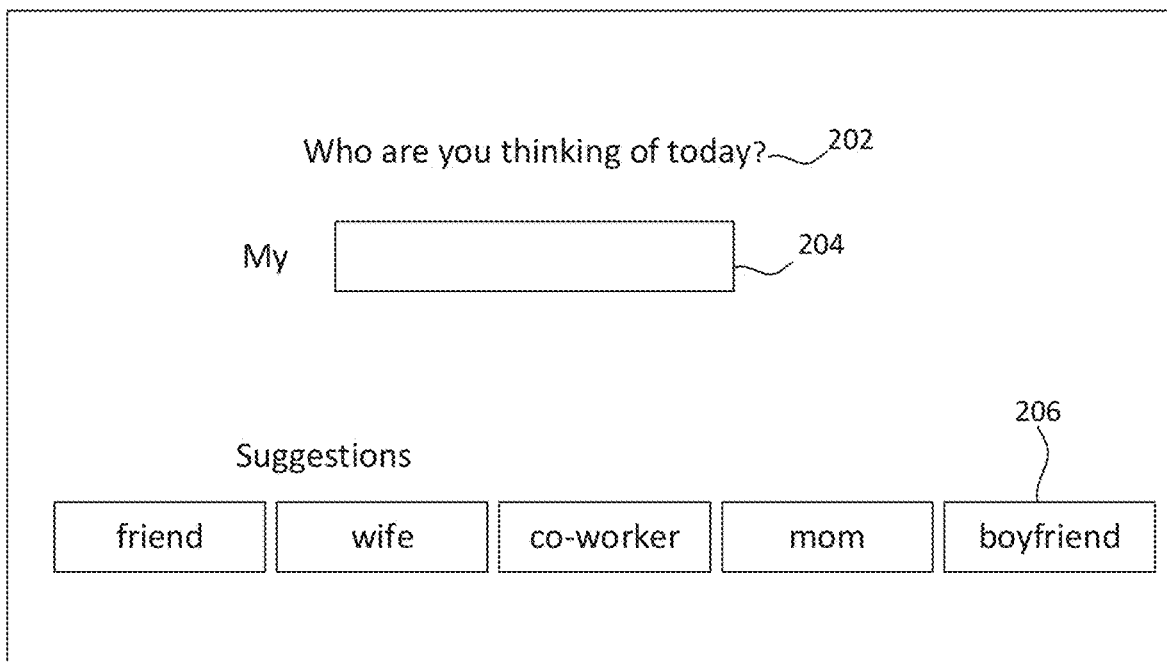
FIGS. 2A-2H depict user interface elements and output appearing as part of an iterative process, in accordance with an embodiment of the present invention.
Figure 2B:
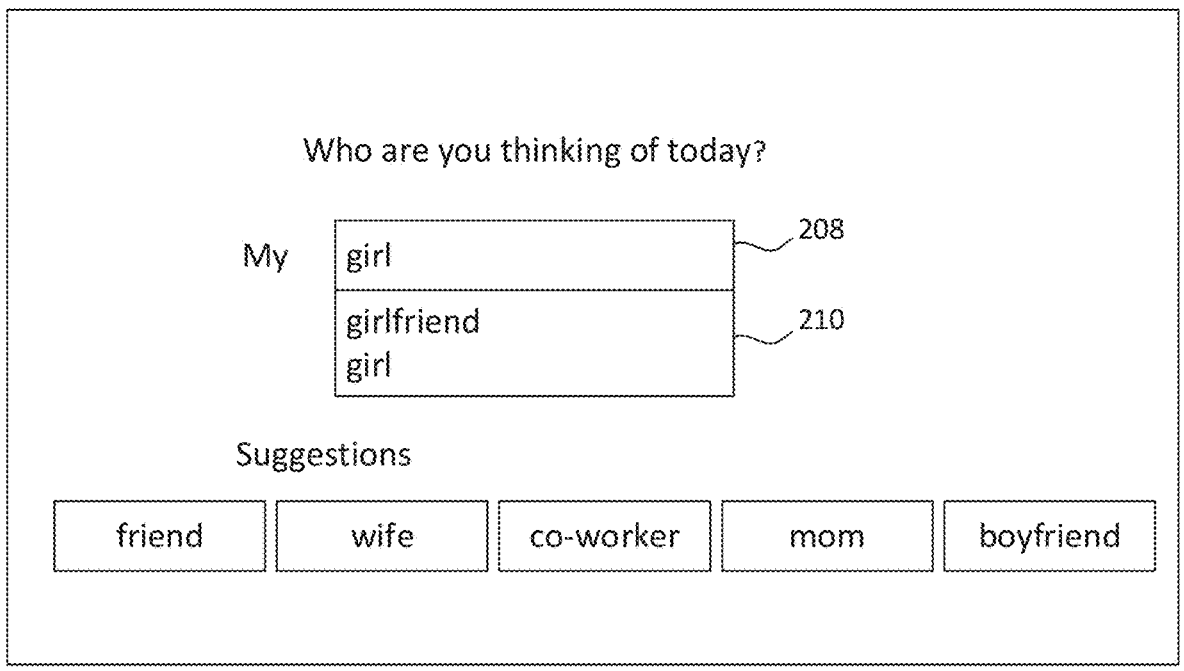

A user experience in accordance with an embodiment of the present invention is depicted in FIGS. 2A-2H which show more specific examples of the elements discussed above. The various elements of the user interfaces of the embodiment presented in these figures can include textual elements such as questions and prompts, static or moving visual image elements including pictures, photographs, and video, as well as interface elements which can be manipulated or engaged to provide user input such as fillable fields, buttons, menus, and selectable item lists. In one version of the invention, a user may initially choose giving a gift (e.g., buying flowers) as the intended purpose of interacting with a software interface of the invention. Then, in a subsequent stage of interaction shown in FIG. 2A, the user may be prompted to provide or identify a relationship 202 with respect to a target individual who is intended to be the beneficiary of the gift. The provision of the relationship can be accomplished by a user completing a fillable field 204, which may include an autocomplete function presenting choices for selection 210 as the user types 208 or otherwise provides input in response to the prompt as shown in FIG. 2B. Alternatively, the provision of relationship information can be realized by a user selecting from a pre-set list of suggestion 206.

Figure 2C:
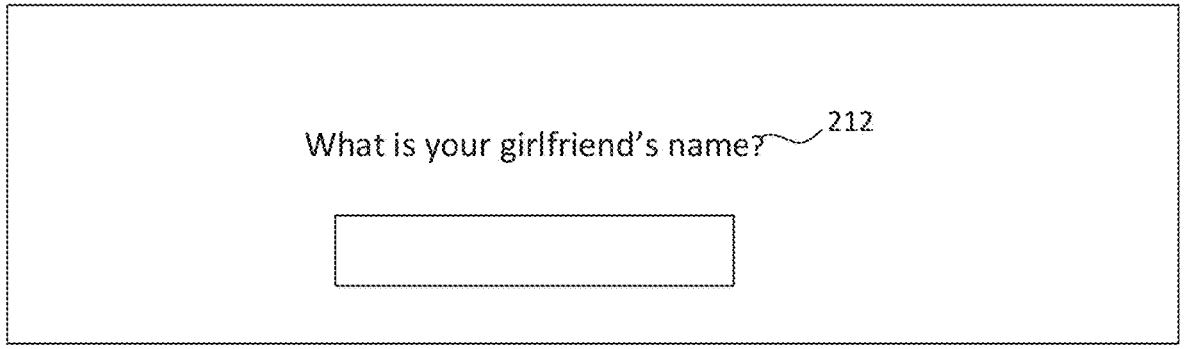
Figure 2D:
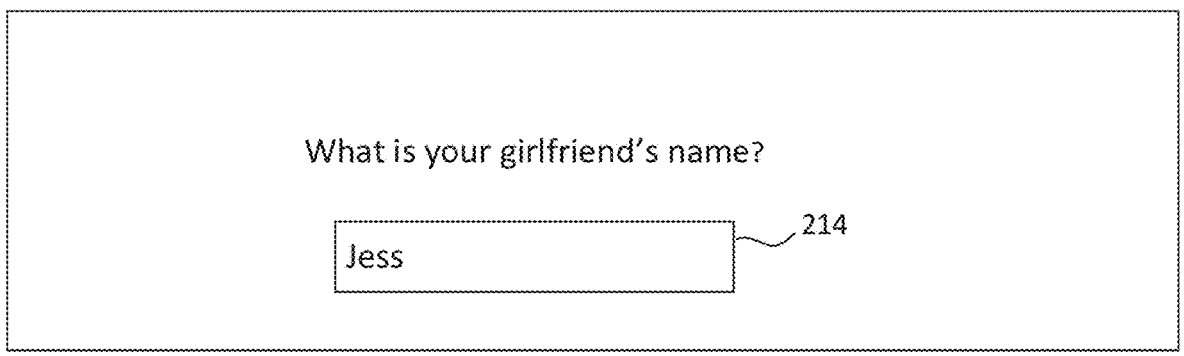

As can be seen in FIG. 2C, in instances where the indication of the user's purpose and relationship to the target individual logically permits, the user may be prompted 212 to provide the target individual's name. The name can be provided by free-form input into field 214 by the user as shown in FIG. 2D. It should be noted that there may be cases where a prompt for the target individual's name may not be applicable such as when the target individual is the user him/herself or when the purpose of interacting with the software interface does not pertain to gift-giving or conveying an emotional message to another individual. Further, it can be seen how the prompt 212 for the target individual's name 212 has been customized to reflect a previous user interaction with a user interface element in a preceding stage. Specifically, the prompt is customized/adapted to refer to a "girlfriend" as a consequence of the user's previous input in response to the prompt to identify the target individual.

Figure 2E:
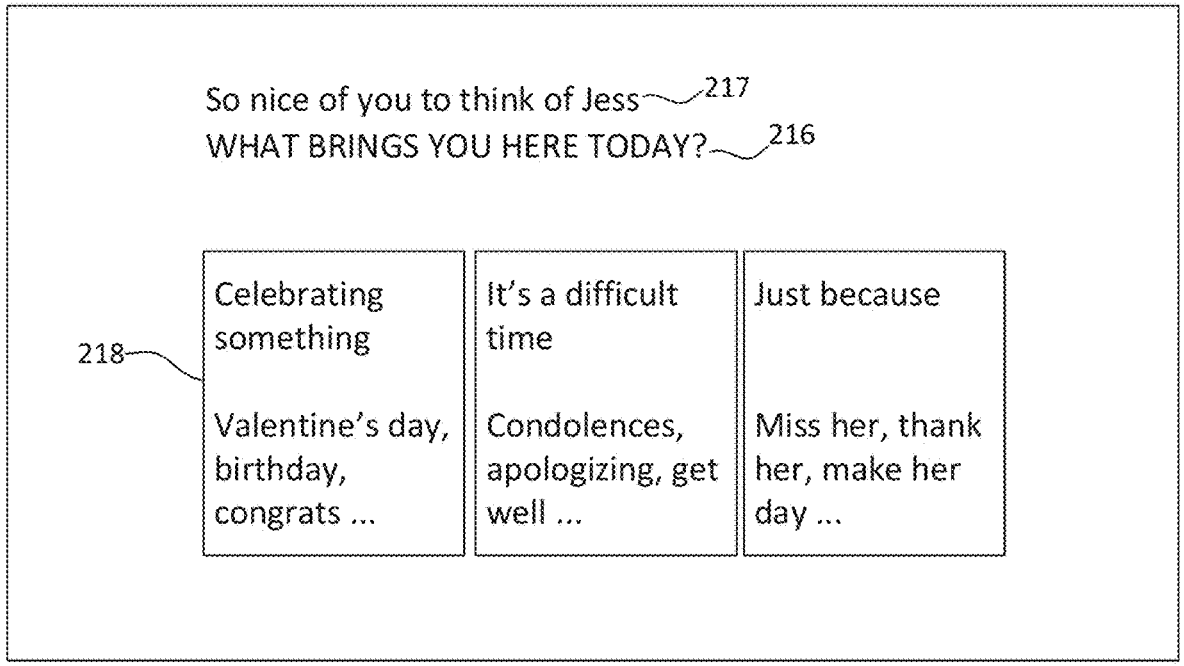

Turning now to FIG. 2E, a user can be presented with an affirmation 217 that is logically related to the input provided previously. In this instance, the affirmation 217 provides an encouraging remark that is logically related to, and emotionally consistent with, the user's input identifying the name 212 of the target individual. The user can also be then prompted, with question 216 or otherwise, to provide one or more root emotion/root reason/root motivator 218. It should be understood that the root motivator 218 corresponds to the root emotion 110 or reason previously discussed with reference to FIG. 1. Although FIG. 2E depicts the identification of the root motivator 218 being achieved by selection from a list of pre-determined options, a person skilled in the art should understand that, just as in the previous descriptions of instances of a user of being prompted for input, the root motivator 218 can be provided by free input into a fillable field, selection from a menu, voice input, as well as other suitable means. It should be noted that one or more root motivators 218 can be selected and that reference to a single root motivator 218 or a plurality of root motivators 218 can be understood as interchangeable herein where logically consistent.

The root motivator can identify the emotional or psychological root of the purpose with which the user is interacting with the embodiment of the invention. As noted earlier, these root motivators 218 can subsequently serve as a basis for presenting customized user interface elements (e.g., prompts, buttons, shapes, fields, selectable lists, etc.) and outputs (text, pictures, shapes, sounds, video, etc.) that are reflective of and/or consistent with the root motivators 218. For example, if the root motivator 218 is related to a somber or sad event or emotion, subsequent elements and outputs may be customized/adapted to be presented in subdued hues reflective of sadness; the number of questions or prompts presented to the user may be small (so as not to unduly burden the user); the verbiage used can be chosen to be sensitive to the sad event; and/or the pictures and tones used can be chosen to be dull or darker. Alternatively, if the root motivator 218 is related to a happy or celebratory occasion, subsequent elements and outputs may reflect this by being presented in bright colorful hues, including a variety of lengthy questions or prompts, and use bright and exciting imagery and tones. In embodiments of the invention solely reliant on audio input and output can have audio output and interface elements include sounds and tonality consistent with an emotional mood or theme represented by the root motivator 218 (e.g., sad sounds and tones of voice prompts for a sad emotional motivator, and cheerful and upbeat sounds and tones for a happy emotional motivator).

Figure 2F:
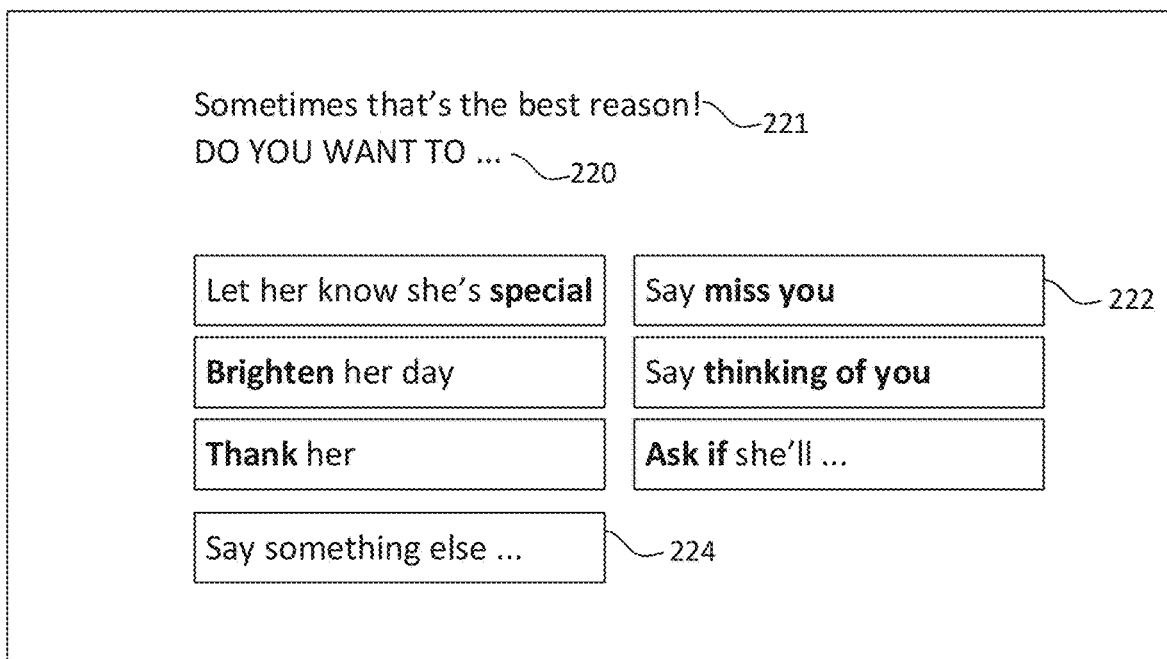

As shown in FIG. 2F, a user can thereafter again be presented with another optional affirmation 221 in response to providing a root motivator 218, which in the instant case was the selection of the "Just Because" option. Notably, the optional affirmation 221 is customized, logically related to, and determined by the input provided at a previous stage of the user's interaction with a user interface element of an embodiment of the invention. The user can also be prompted with a question or an open ended phrase 220 to provide more specific information regarding the user's emotional intent or goal. Conceptually, this aspect of the invention can be understood to be a narrowing of the emotional funnel as the user is guided to an ever more precise articulation of the user's emotional goal. Thus, in response to the prompt a user can select a more precise emotional intent from a pre-determined list 222 that is derived from, dependent on, and consistent with the root motivator(s) 218 and previous inputs provided by the user. Alternatively, the user can also freely input a response into fillable field 224 to more precisely describe the user's emotional intent. It should be understood that this response indicating a more precise emotional intent corresponds to the main reason 118 discussed previously with reference to FIG. 1.

Figure 2G:
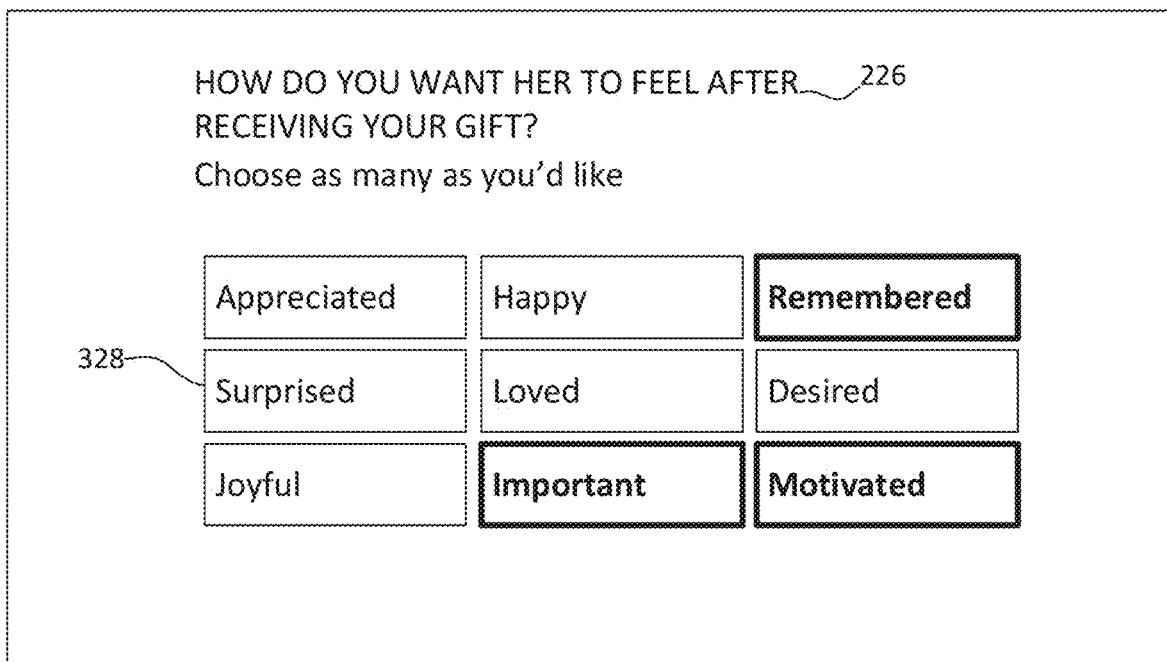

Thereafter, as depicted in FIG. 2G a user can be presented with an additional prompt 226 for provision of information that can even further specify or assist in articulating the user's emotional intent. Note that the user's emotional intent can be defined in terms of how the user desires for the target individual to feel which may not necessarily be congruent with the user's emotional state or condition. Accordingly, a user can provide input further specifying the user's emotional intent by selecting from a list of pre-selected options 228 or providing textual, tactile, or voice input including information that is responsive to the additional prompt 226. It should be understood that in the various embodiments described herein the iterative process depicted in FIGS. 2A-2G can be repeated or conducted in an order other than the one described herein. In some embodiments, alternatively to or in addition to questions/prompts, information concerning a user's reasons or emotional goal may be obtained through facial recognition, gesture recognition, and/or voice signature analysis. Because a user's non-verbal communication, cues, involuntary reflexes/cues, as well as the tone/timbre of their voice may be indicative of their emotional state or emotional intent with respect to a target individual, the information obtained through these alternative means can be used in conjunction with, or in lieu of, the information obtained through the questions/prompts.

Figure 2H:
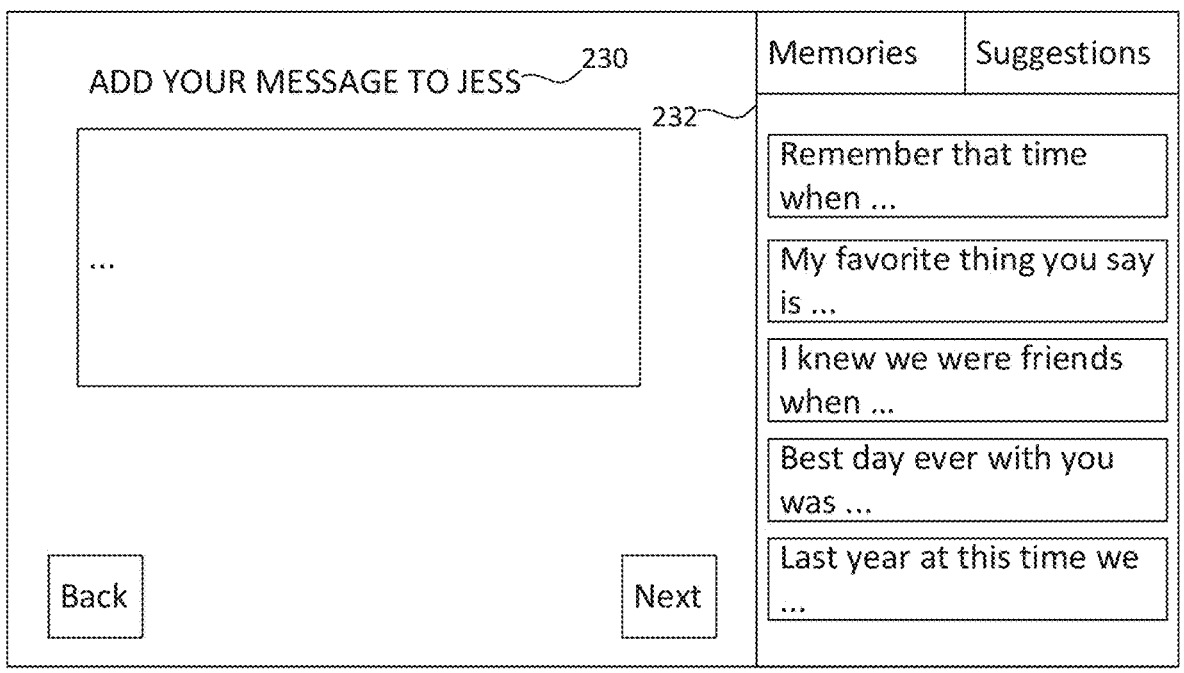

Thus, having provided at least one root motivator 218 and having gone through an iterative emotional funnel process with elements and outputs correspondent with either the root motivator 218 and/or the main reason 118 and achieving the desired level of precision in articulating or eliciting the user's emotional-goal, the user can then be provided with suggestions or recommendation relating to the fulfillment of that goal. As can be seen in FIG. 2H, a user can be presented with a suggestions of including a message 230 to be sent to the target individual that accurately conveys the emotional goal. In some embodiments, pre-made recommendations or suggestions 232 of message content can be presented to the user based on either the root motivator 218 and/or one or more inputs provided by the user at an earlier stage of the iterative process. In other embodiments, the user may be presented with recommendations of multimedia (e.g., audio, video, or audio-video) content to send to the target individual that coveys an emotional message consistent with the user's emotional goal. In this manner the present invention can assist the user in fulfilling the user's emotional goal by priming the user to write a better card message than the user would have otherwise written by having identified the emotional goal with sufficient precision prior to writing the message.

Figure 3:
FIG. 3 shows a recommendation aimed at fulfilling a user's emotional goal, in accordance with an embodiment of the present invention.

In another embodiment, seen in FIG. 3, a user can be presented with product or service suggestions 350 that are aimed at fulfilling the user's previously identified emotional goal. It should be noted that, the presentation of the suggested product or service is an extension of the user's interaction with the software interface of the embodiment and contains elements and outputs representative or reflective of the user's root motivator 218, of any intervening user-inputs and selections, and/or of the specific emotional goal. Accordingly, the recommendation of a product may include a product name 352 that stems from, and is dependent on, an input provided by a user at an earlier time (e.g., by incorporating the name of the target recipient of the product in the product's name). Further, the product recommendation, the message as described in FIG. 2H, as well as multimedia content recommended to be conveyed to the target individual to fulfill the emotional goal, can also include a dynamically depicted inspiration sentence fragments 356 or suggestion sentence fragments that relate to or describe the motional goal. The presentation of a product recommendation to the user can also include other descriptive textual 354 and/or pictorial 346 outputs provided to the user that are semantically, tonally, thematically, or chromatically related to the root motivator(s) 218, intervening inputs and selections, and/or to the specific emotional goal.

Because a potential user's emotional-goal cannot be suitably captured by conventional approaches to emotional message composition or gift product selection, embodiments of the invention incorporate a multifaceted logical structure that enables a user to hone in on their desired emotional goal through an iterative process that can be depicted as a logical tree diagram. Exemplary tree diagrams of a user proceeding through the iterative process described above are shown in FIGS. 4A-4E. Each of the figures show a plurality of logical paths that can be followed from an initially identified core motivator to a specific ultimate emotional goal along with intervening stages of the iterative narrowing and specification of the emotional goal that occur along the way.

As mentioned earlier, the methods and systems described herein are contemplated to be used together with a variety of different core motivators, main reasons, and sub-reasons to arrive at a sufficiently specific emotional-goal and a suggestion pertaining to the fulfillment of that goal. It should be understood that the intervening stages of iterative narrowing and specification can include an arbitrary number of reasons 118 and sub-reasons 120 described above with reference to FIG. 1. Core motivators can be defined broadly and can include but are not limited to core motivator indications such as "Thinking of You" 402 shown in FIG. 4A, "Romance" 416 shown in FIG. 4B, "Celebrating!" shown in FIG. 4C, "Feeling Thankful" shown in FIG. 4D, and "Other" shown in FIG. 4E. Considering that the iterative process of ascertaining a user's emotional-goal can terminate at an arbitrary level of precision, the paths that a user may take through the iterative process may be different in length depending on the user's root motivator(s) 218, the level of desired specificity, and the number of times the user chooses to undergo the iterative process of the emotional funnel. For example, a user may begin the process by indicating that with respect to a given target individual the user is "Thinking of You" 402. Afterwards, a user may be presented with a series of optional affirmations as well as with prompts and/or questions attempting to elicit more precise emotional information from the user. After two iterative presentations of a prompt/ question, the user may specify that the user is thinking of the target individual because the target individual is "Going through hard stuff" 404 (e.g., the death of a loved one) and that the user desires to express "Sympathy" 406 to the target individual. Through additional questions/prompts and responses or inputs provided, the user can be guided to specify that the emotional goal of the user includes a "Celebration of Life" 408 that is "Honoring" 410 the life of the individual regarding whose loss the user wants to console the target individual. Alternatively, the level of precision of determining the emotional goal can be low resulting in a short path along the logical tree. For example, a root motivator of "Thinking of You" 402 can be further specified with only one iteration of prompts/questions to identify that the user has the emotional goal of saying "Good Luck" 412 to the target individual. As further described below, some paths 414 through the iterative process originating with one root motivator 218 can overlap or coincide with paths originating with other root motivators and result in similar emotional-goals being identified.

Figure 4A:
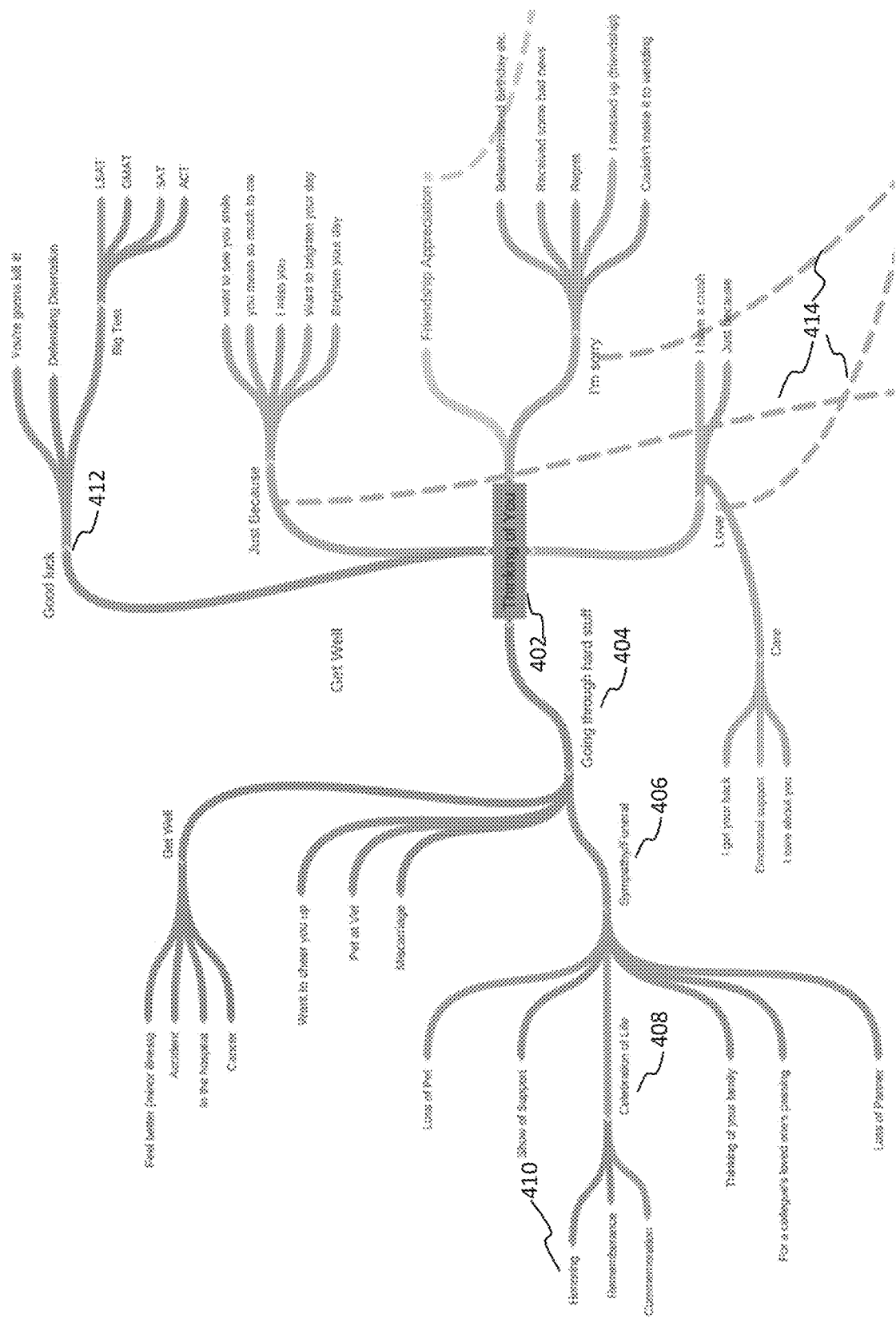
FIGS. 4A-4E depict logical tree diagrams, in accordance with an embodiment of the present invention.
Figure 4B:
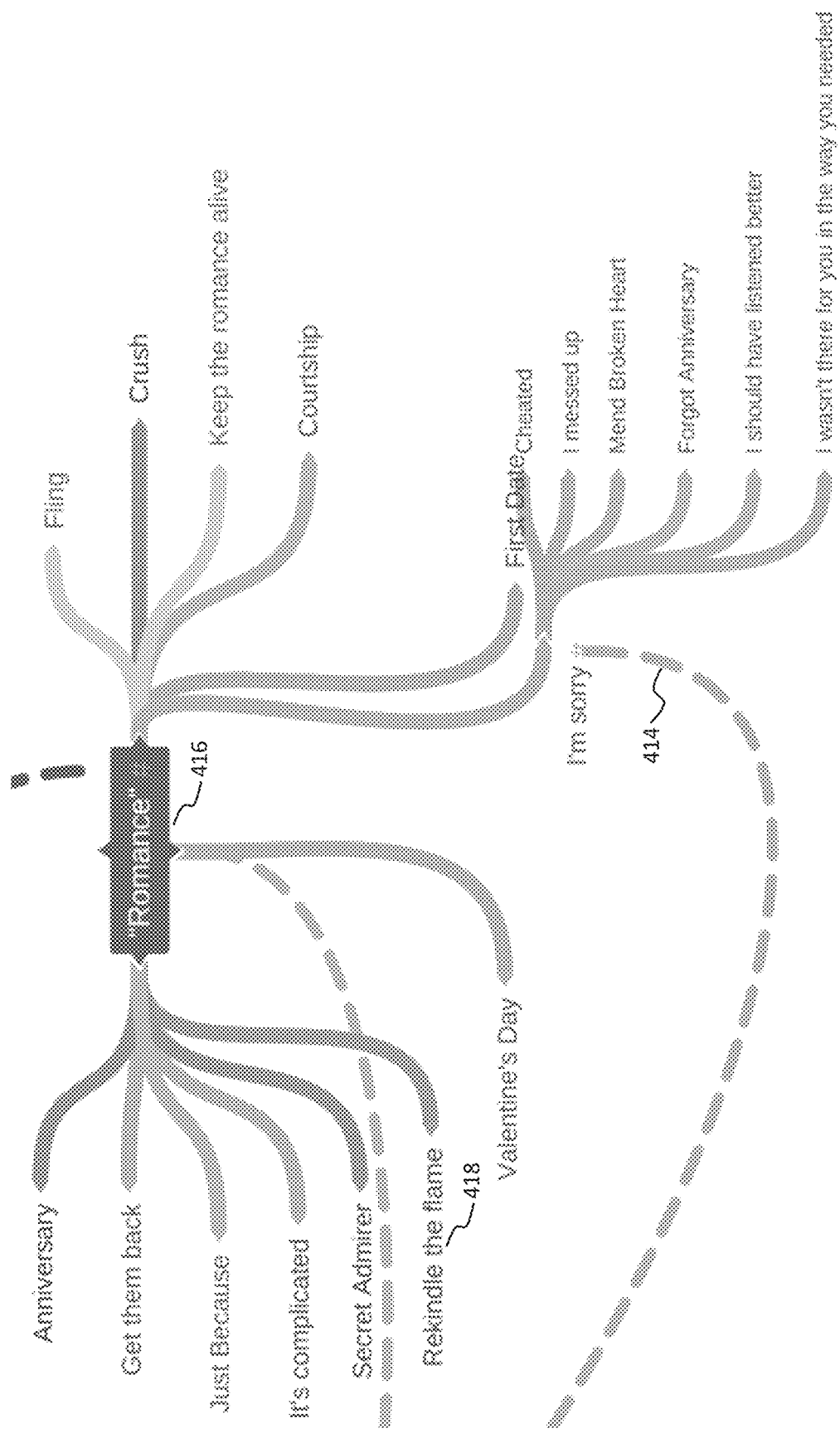

For example, as seen in FIG. 4B, a path leading from the root motivator of "Romance" 416 may include a single main reason 118, namely "Rekindle the flame" 418, that sufficiently specifies the user's emotional goal. The same root motivator "Romance" 416 can include a path 414 that overlaps with the path 414 originating with the "Thinking of you" 402 root motivator.

Figure 4C:
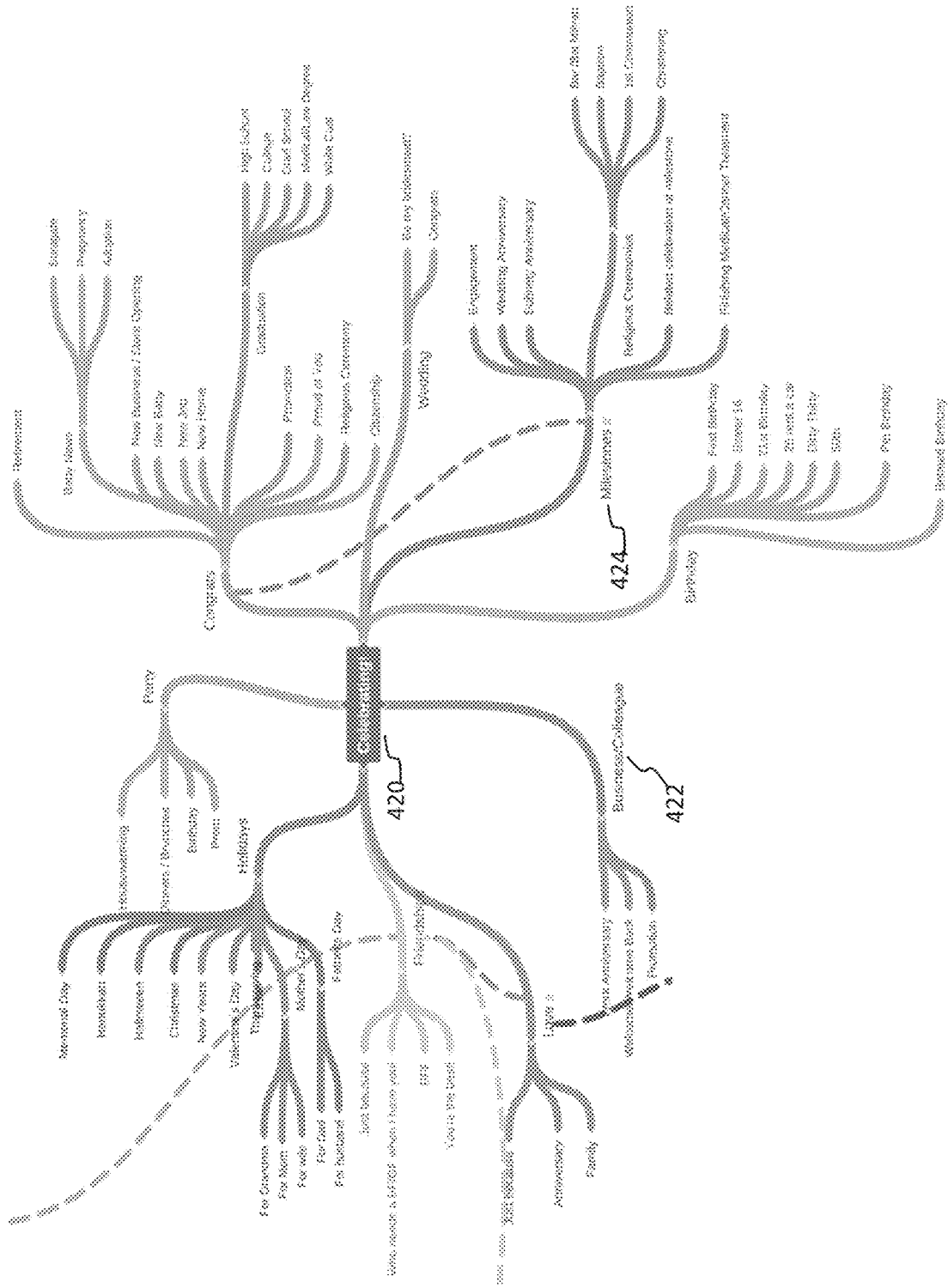
Figure 4D:
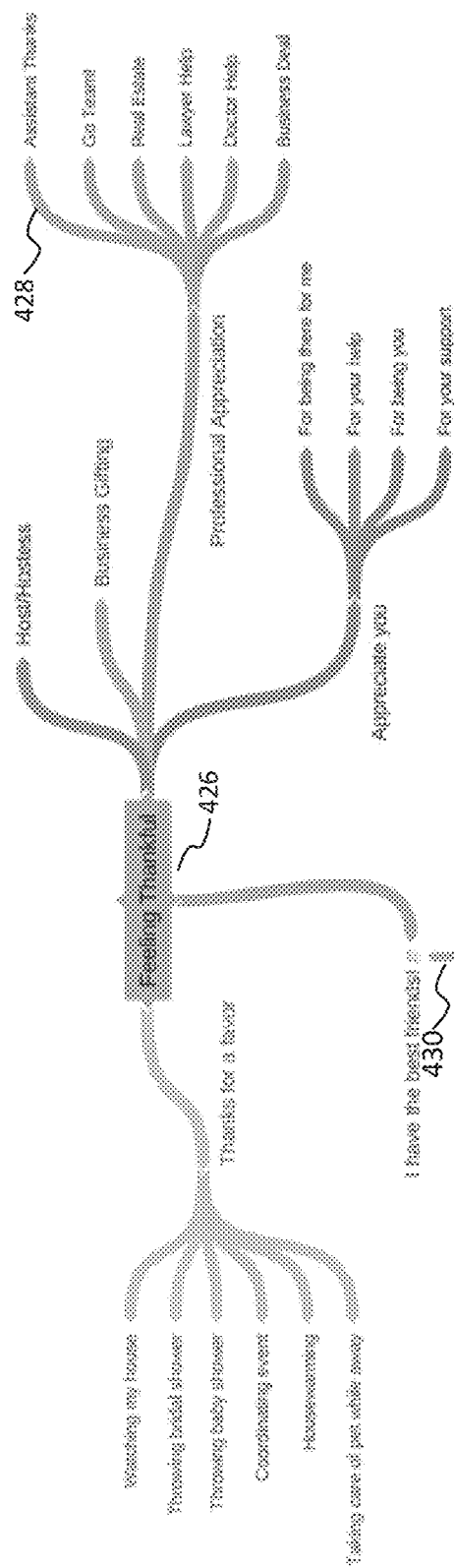
Figure 4E:
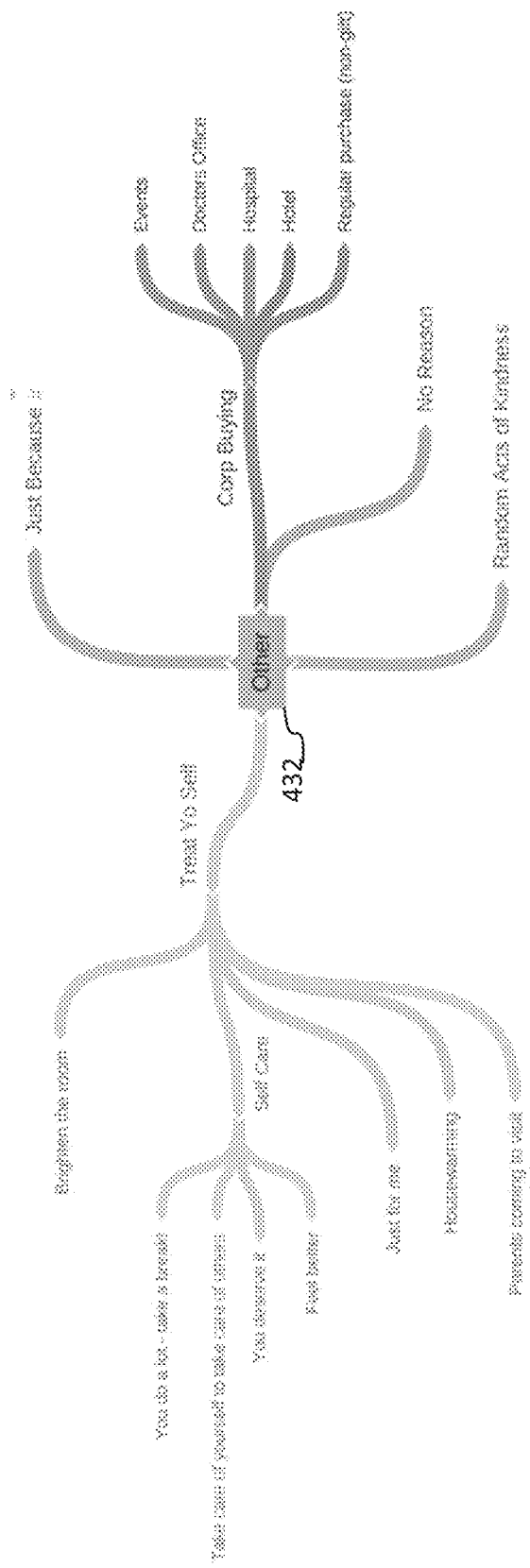

Further, it should be understood that despite there being further potential for additional refinement and specification of an emotional goal through interaction with the software interface of an embodiment, a user may choose to end the iterative process of more precisely defining the emotional goal at a lower level of specificity. As shown in FIG. 4C, a user beginning with a root motivator of "Celebrating!" 420 can choose to end the process after one set of prompts/ questions and be satisfied with specifying the goal by narrowing the identified emotional intent to celebrating "Colleagues" 422 or celebrating a "milestone" 424 without going any further. It should be noted that an emotional goal defined at a low level of precision can result in a suggestion or recommendation that is tailored to the emotional goal to a correspondingly low level of precision.

The above described methods of the embodiments of the present invention can be performed on a single computing device, a set of interlinked computing devices, or embodied as computer readable and/or executable instructions on a non-transitory computer readable medium. It should be understood that the computer readable program instructions may execute entirely on a user's computing device, partly on the user's computing device, as a stand-alone software package, partly on the user's computer and partly on a remote computing device (e.g., a server), or entirely on a remote computing device or server. In the latter scenario, the remote computing device may be connected to the user's computing device through any type of network, including a local area network (LAN) or a wide area network (WAN), or the connection may be made to an external computing device (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the invention.

According to an exemplary embodiment of the invention, data may be transferred to the system, stored by the system and/or transferred by the system to users of the system across LANs (e.g., office networks, home networks) or WANs (e.g., the Internet). In accordance with such an embodiment, the system may be comprised of numerous computing devices and/or numerous servers communicatively connected across one or more LANs and/or WANs. For example, there may be a hand-held computing device being operated by a user to send input and selections via the internet to a server to generate a series of questions/prompts on the display of the hand-held device. Alternatively an audio computing device can be operated by a user's voice to send input and selections via the internet to a server to generate a series of questions/prompts to be presented to a user via audio. One of ordinary skill in the art would appreciate that there are a variety of ways in which the system could be configured, and embodiments of the invention are contemplated for use with any such configuration.

In general, the system and methods provided herein may be employed by a user of a computing device whether connected to a network or not. Similarly, some steps of the methods provided herein may be performed by components and modules of the system whether connected or not. While such components/modules are offline, and the data they generated will then be transmitted to the relevant other parts of the system once the offline component/module comes again online with the rest of the network (or a relevant part thereof). For example, a user may be operating a tablet device to input responses and selections after being presented with prompts/questions to arrive at a precise articulation of the user's emotional-goal and have the table generate a customized recommendation for fulfilling the user's emotional goal without needing the tablet to be connected to the internet. Therefore, in some embodiments, some of its applications, features, or functions may not be accessible when not connected to a network, however a user or a module/component of the system itself may be able to compose, combine, or generate data offline from the remainder of the system that will be consumed by the system or its other components when the user/offline system component or module is later connected to the system network.

Figure 5:
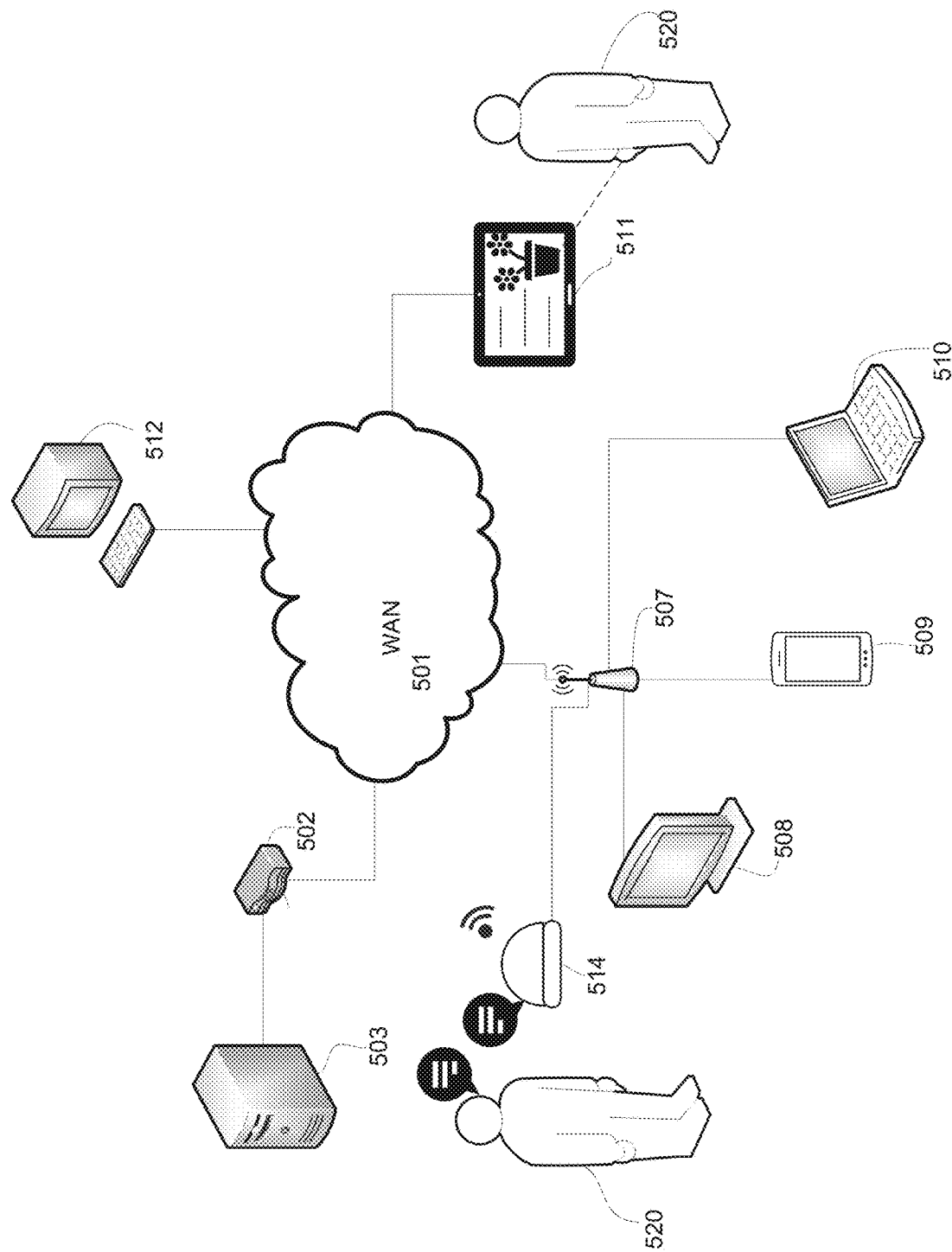
FIG. 5 depicts a schematic diagram of a networked system, in accordance with an embodiment of the present invention.

Referring to FIG. 5, a schematic overview of a system in accordance with an embodiment of the invention is shown. The system can be comprised of one or more application servers 503 for electronically storing information used by the system. Applications in the server 503 may retrieve and manipulate information in storage devices and exchange information through a WAN 501 (e.g., the Internet). Applications in server 503 may also be used to manipulate information stored remotely and process and analyze data stored remotely across a WAN 501 (e.g., the Internet).

According to an exemplary embodiment, as shown in FIG. 5, exchange of information through the WAN 501 or other network may occur through one or more high speed connections. In some cases, high speed connections may be over-the-air (OTA), passed through networked systems, directly connected to one or more WANs 501 or directed through one or more routers 502. One of ordinary skill in the art would appreciate that there are numerous ways server 503 may connect to WAN 501 for the exchange of information, and various embodiments of the invention are contemplated for use with any method for connecting to networks for the purpose of exchanging information.

Components, elements, or modules of the system may connect to server 503 via WAN 501 or other network in various ways. For instance, a component or module may connect to the system (i) through a computing device 512 directly connected to the WAN 501, (ii) through a computing device connected to the WAN 501 through a routing device 502, (iii) through a computing device 508, 509, 510, 514 connected to a wireless access point 507, or (iv) through a computing device 511 via a wireless connection (e.g., WiFi, CDMA, GMS, 3G, 4G, 5G, other suitable means, and means not yet invented) to the WAN 501. One of ordinary skill in the art will appreciate that there are numerous ways that a component or module may connect to server 503 via WAN 501 or other network, and embodiments of the invention are contemplated for use with any method for connecting to server 503 via WAN 501 or other network. Furthermore, server 503 could be comprised of a personal computing device, such as a smartphone or tablet, acting as a host for other computing devices to connect to.

Users 520 of the system in accordance with embodiments of the invention can interact with the system via computing devices such as a laptop 510, personal computers 508, cell phones/smart phones 509, tablets 511, smart speakers 514, smart TVs, smart hubs, smart kiosks, and the like. Each of the abovementioned steps and aspects can be performed via the input and output means of these respective devices including presentation of software user interface elements, presentation of prompts/questions to the user, collection of user input, presentation of options, suggestions, and recommendations, as well as the subsequent presentation of recommended courses of action, products, or services aimed at achieving the user's emotional goal. For example, a user 520 can operate a tablet 511 to navigate to a browser interface presenting a web-based version of the software interface of the invention and be presented with prompts and questions on the screen of the laptop in response to which the user can provide inputs via the touchscreen of the tablet.

Consequently, the tablet 511 can provide iteratively more narrow questions and prompts to determine the user's emotional goal by processing the user input locally or having it, in whole or in part, be sent to be processed on a remote device such as a server, to then have a customized recommendation for the fulfillment of that emotional goal be generated on the screen of the tablet 511. It should be understood that the user can interact with the software interface of the invention by engaging user interface elements and entering input through a touch-screen of the tablet 511.

Alternatively, in an embodiment of the invention incorporating an audio device such as a smart speaker 514, a user can initialize an audio software interface to receive audio output and provide audio input to interact with the interface elements. For example, upon initializing a smart speaker 514 application version of the invention, user 520 can be presented with prompts, questions and other requests for input or selections via the audio output a smart speaker 514 (e.g., through statements or questions being presented through a voice emanating from the smart speaker 514). Thereafter, the user 520 can provide input in response to the prompts/question and make selections from among the options and suggestions via voice input.

It should be understood by a person skilled in the art that the aforementioned collection of facial or gesture information can be realized through the use of image capture devices (e.g., camera(s) on a smart phone 209, laptop 210, tablet 211, computer 205 configured with a webcam, smart hubs, smart kiosks etc.) included in a system or device in accordance with an embodiment of the invention. Analogously, the collection of voice information in accordance with the various embodiments can be performed through the use of a microphone or other suitable sound capture and recording device that may be included on a variety of devices such as a smart phone 209, laptop 210, tablet 211, computer 205, a smart speaker 214, and the like.

The communications means of the system, according to embodiments of the present invention, may be any means for communicating data, including image and video, over one or more networks or to one or more peripheral devices attached to the system, or to a system module or component. Appropriate communications means may include, but are not limited to, wireless connections, wired connections, cellular connections, data port connections, Bluetooth® connections, or any combination thereof. One of ordinary skill in the art will appreciate that there are numerous communications means that may be utilized with embodiments of the invention, and embodiments of the invention are contemplated for use with any communications means.

Traditionally, a computer program includes a finite sequence of computational instructions or program instructions. It will be appreciated that a programmable apparatus or computing device can receive such a computer program and, by processing the computational instructions thereof, produce a technical effect. It should be understood that a programmable apparatus or computing device can include one or more microprocessors, microcontrollers, embedded microcontrollers, programmable digital signal processors, programmable devices, programmable gate arrays, programmable array logic, memory devices, application specific integrated circuits, or the like, which can be suitably employed or configured to process computer program instructions, execute computer logic, store computer data, and so on. Throughout this specification and elsewhere, a computing device can include any and all suitable combinations of at least one general purpose computer, special-purpose computer, programmable data processing apparatus, processor, processor architecture, and so on.

Any combination of one or more computer readable medium(s) may be utilized with the various embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. Illustrative examples of the computer readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, a static random access memory (SRAM), a digital versatile disk (DVD), a memory stick, a floppy disk, a mechanically encoded device such as punch-cards or raised structures in a groove having instructions recorded thereon, and any suitable combination of the foregoing.

Computer readable program instructions described herein can be downloaded to respective computing/processing devices from a computer readable storage medium or to an external computing device or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The flowchart and block diagrams in the Figures illustrate the architecture, functionality, and operation of possible implementations of systems, methods, and computer program products according to the various embodiments hereof. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the figures.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Figure 6:
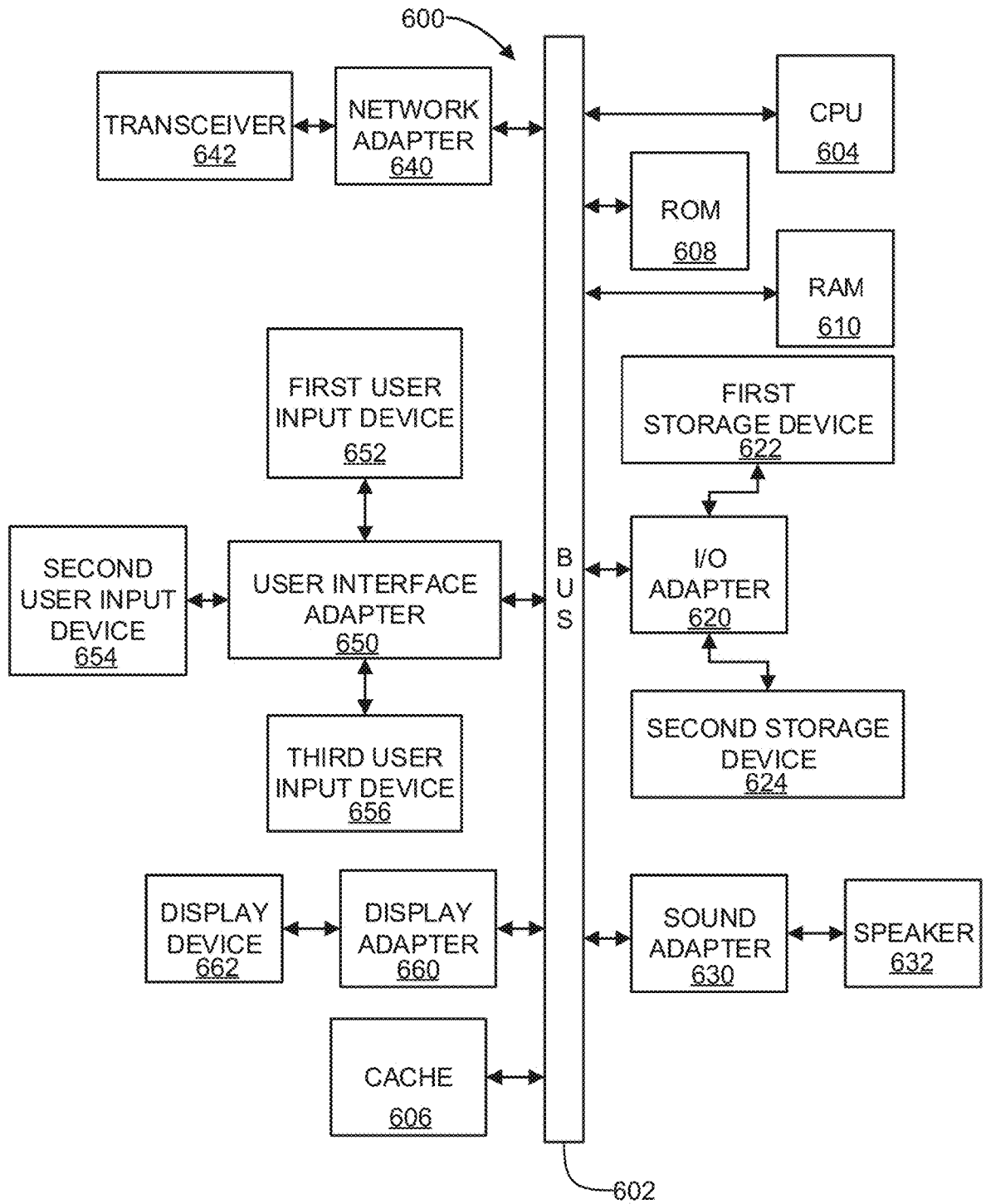
FIG. 6 shows a schematic diagram of a system, in accordance with an embodiment of the present invention.

As noted earlier, the methods described above as well as the exemplary web-interface based system may be implemented on a variety of computing devices or processing systems. An illustrative representation of an exemplary computing device/processing system in accordance with an embodiment of the present invention is shown in FIG. 6. The computing device 600 can generally be comprised of a Central Processing Unit (CPU) 604 operatively coupled to other components via a system bus 602, optional further processing units including a graphics processing unit (GPU), a cache, a Read Only Memory (ROM) 608, and a Random Access Memory (RAM) 610. The computing device 600 can also include an input/output (I/O) adapter 620, a sound adapter 630, a network adapter 640, a user interface adapter 650, and a display adapter 660, all of which may be operatively coupled to the system bus 602.

Additionally, a first storage device 622 and a second storage device 624 can be operatively coupled to system bus 602 by the I/O adapter 620. The storage devices 622 and 624 can be any of a disk storage device (e.g., a magnetic or optical disk storage device), a solid state magnetic device, and so forth. It should be appreciated that the storage devices 622 and 624 can be the same type of storage device or different types of storage devices. In instances where the device 600 is embodied by a smart speaker 214 or the like, it can incorporate a speaker 632 which may be operatively coupled to system bus 602 by the sound adapter 630. A transceiver 642 may be operatively coupled to system bus 602 by network adapter 640. In instances where the device 600 is embodied by a tablet 511 or a smart phone 509, it can include a display device 662 which may be operatively coupled to system bus 602 by display adapter 660.

In some embodiments, the device 600 may include a mother board, alternatively/additionally a different storage medium (e.g., hard disk drive, solid state drive, flash memory, cloud storage), an operating system, one or more application software and one or more input/output devices/ means, including one or more communication interfaces (e.g., RS232, Ethernet, Wifi, Bluetooth, USB). Accordingly, in some embodiments a first user-input device 652, a second user-input device 654, and a third user-input device 656 may be operatively coupled to system bus 602 by user interface adapter 650. The user-input devices 652, 654, and 656 can be any of a keyboard, a mouse, a keypad, an image capture device (e.g., a camera), a motion sensing device, a microphone, a touch-sensitive device (e.g., a touch screen or touchpad), a device incorporating the functionality of at least two of the preceding devices, and so forth. Of course, other types of input devices can also be used, while remaining within the scope and spirit of the present invention. The user-input devices 652, 654, and 656 can be the same type of user-input device or different types of user-input devices. The user-input devices 652, 654, and 656 may be used to input and output information to and from system 600.

Thus, the prompts and questions discussed above may be presented to the user via the output means of exemplary device 600 in accordance with the embodiments of the present invention. Whether visually via a display device 662, audibly via speaker 632, or through a combination of both, a user can be prompted to respond to questions, enter input, or make selections in accordance with an embodiment of the invention. Accordingly, whether through tactile, audio, or video input through input devices 652, 654, and 656 a user can provide the input and selections to interact with the various elements and aspects of the invention to provide the information used for ascertaining a user's emotional goal and providing recommendations regarding the fulfillment of that emotional goal.

Of course, the processing system/device 600 may also include other elements (not shown), as readily contemplated by one of skill in the art, as well as omit certain elements. For example, various other input devices and/or output devices can be included in processing system 600, depending upon the particular implementation of the same, as readily understood by one of ordinary skill in the art. For example, various types of wireless and/or wired input and/or output devices can be used and additional processors, controllers, memories, and so forth, in various configurations can also be utilized as readily appreciated by one of ordinary skill in the art. These and other variations of the processing system 600 are readily contemplated by one of ordinary skill in the art given the teachings of the embodiments provided herein.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

It will be appreciated that computer program instructions may include computer executable code. Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including a functional programming language such as python, an object oriented programming language such as SMALLTALK, C++ or the like, and conventional procedural programming languages, such as the "C" programming language or similar programming languages. A variety of languages for expressing computer program instructions are possible, including without limitation, Java, JavaScript, assembly language, Lisp, HTML, Perl, and so on. Such languages may include assembly languages, hardware description languages, database programming languages, functional programming languages, imperative programming languages, and so on. In some embodiments, computer program instructions can be stored, compiled, or interpreted to run on a computing device, a programmable data processing apparatus, a heterogeneous combination of processors or processor architectures, and so on. Without limitation, embodiments of the system as described herein can take the form of web-based computer software, which includes client/server software, software-as-a-service, peer-to-peer software, or the like.

As employed herein, the term "hardware processor subsystem", "hardware processor", "processing device", or "computing device" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs). These and other variations of a hardware processor subsystem are also contemplated in accordance with embodiments of the present invention.

Unless explicitly stated or otherwise clear from the context, the verbs "process" and "execute" are used interchangeably to indicate execute, process, interpret, compile, assemble, link, load, any and all combinations of the foregoing, or the like. Therefore, embodiments that process computer program instructions, computer-executable code, or the like can suitably act upon the instructions or code in any and all of the ways just described.

The functions and operations presented herein are not inherently related to any particular computing device or other apparatus. Various general-purpose systems may also be used with programs in accordance with the teachings herein, or it may prove convenient to construct more specialized apparatus to perform the required method steps.

Throughout this specification and elsewhere, block diagrams and flowchart illustrations depict methods, apparatuses (e.g., systems), and computer program products. Each element of the block diagrams and flowchart illustrations, as well as each respective combination of elements in the block diagrams and flowchart illustrations, illustrates a function of the methods, apparatuses, and computer program products. Any and all such functions ("depicted functions") can be implemented by computer program instructions; by special-purpose, hardware-based computer systems; by combinations of special purpose hardware and computer instructions; by combinations of general purpose hardware and computer instructions; and so on—any and all of which may be generally referred to herein as a "component", "module," or "system."

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims.

What is claimed is:

1. A computer implemented method for ascertaining a user's emotional goal, comprising:
    receiving, via an emotionally responsive computerized system having a user interface communicatively coupled to a networked user device having a processor device, a first user-input indicating a purpose of a user's interaction with a software interface;
    registering a second user-input indicative of a target person to whom the purpose of the user's interaction pertains after receiving the first user-input;
    prompting a user to provide at least one root motivator for the interaction after registering the second user-input;
    generating a visual, audio, or audio-visual output and a set of user interface elements dependent on the at least one root motivator;
    presenting a sequence of user interface elements that are associated with the root motivator and with the second user-input, after generating the set of user interface elements dependent on the at least one root motivator, wherein a sentiment is indicated or implied by at least one of the fist user-input and the second user input;
    prompting the user, via a first user element of the sequence, to indicate a main reason specifying an emotional intent that is conceptually narrower relative to the root motivator, wherein the emotional intent is defined relative to how the target person is desired to feel;
    prompting the user, via a second user element of the sequence, to provide a sub reason in support of the main reason;
    presenting at least one affirmation responsive to at least one user-input, wherein the at least one affirmation is reflective of the sentiment that is indicated by the at least one user-input;
    repeating an iterative process of affirming a previous user-input and prompting the user to provide more details specifying the emotional intent until a desired level of precision in determining the user's emotional goal is reached, wherein the desired level of precision is determined by a chosen number of times to repeat the iterative process; and
    responsive to the desired level of precision being reached, obtaining the user's emotional goal with respect to t he target person, based on the second user-input, the at least one root motivator, the main reason, and the sub reason, to provide the user, via the software interface, a recommendation regarding a fulfillment of the user's emotional goal.

2. The method of claim 1, wherein generating the user-perceptible output and the set of user interface elements comprises generating at least one output and a plurality of elements in the set of user interface elements wherein the at least one output and the plurality of elements prompt the user to provide information specifying the emotional intent, and wherein the at least one output and the plurality of elements are each reflective of a theme consistent with the at least one root motivator, such that the at least one output and the plurality of elements are each consistent with the root motivator by color, hue, or a combination thereof.

3. The method of claim 2, wherein generating output and elements reflective of a theme consistent with the at least one root motivator comprises generating images and sounds that are respectively semantically, tonally, thematically, and chromatically related to the at least one root motivator.

4. The method of claim 1, wherein generation of a subsequent user interface element and generation of a subsequent output are respectively dependent, at least in part, on a preceding user interface element interaction, and wherein a subsequent user-input is of a different type than a preceding user-input, wherein at least one user-input is a free-form fillable field input.

5. The method of claim 1, wherein each subsequent user interface element in the sequence presented to the user that includes a prompt or a query elicits a more precise description of the user's emotional goal with higher specificity than the description elicited by a preceding prompt or query, wherein the main reason provides more specific details regarding the emotional intent of the user provided by the root motivator, and wherein the sub reason supports the main reason by specifying a conceptually narrower articulation of the emotional intent of the user.

6. The method of claim 1, wherein a length of the iterative process depends on the desired level of precision and on a number of iterations of sequential affirmations and prompts presented to the user.

7. The method of claim 1, wherein an emotion associated with the root motivator is different than the emotion intended to be conveyed by the user's emotional goal.

8. The method of claim 1, wherein the sequence of user interface elements comprises a plurality of affirmations that comprises the at least one affirmation, wherein each affirmation of the plurality of affirmations is associated with a data node in a data structure and a data value, the data structure defining relationships between data nodes, and wherein each affirmation is associated with a preceding user-input.

9. The method of claim 1, wherein a number of elements in the sequence of user interface elements depends on the at least one root motivator and the second user-input.

10. A non-transitory computer readable medium embodying instructions executable by a computing device which when executed cause the computing device to:
- register a first user-input indicating a purpose of a user's interaction with a software interface of the computing device;
- register a second user-input indicative of a target person to whom the purpose of the user's interaction pertains after registering the first user-input;
- prompt a user to provide at least one root emotion for the interaction after registering the second user-input;
- generate a visual, audio, or audio-visual output and a set of user interface elements dependent on the at least one root emotion;
- present a sequence of user interface elements that are associated with the root emotion and with the second user-input, after generating the set of user interface elements dependent on the at least one root emotion;
- prompt the user, via a first user element of the sequence, to indicate a main reason in support of the at least one root emotion;
- prompt the user, via a second user element of the sequence, to provide a sub reason in support of the main reason;
- receive, a series of user-inputs wherein relative to a preceding user-input, a subsequent user-input further specifies an emotional intent that is conceptually narrower relative to the root emotion of the user, wherein the emotional intent is defined relative to how the target person is desired to feel;
- repeat an iterative process of affirming a previous user-input and prompting the user to provide more details specifying the emotional intent until a desired level of precision in determining the user's emotional goal is reached, wherein the desired level of precision is determined by a chosen number of times to repeat the iterative process; and
- responsive to the desired level of precision being reached, obtain the user's emotional goal with respect to the target person based on the second user-input, on the at least one root emotion, and on user-inputs provided via the sequence of user interface elements, to provide the user, via the software interface, a recommendation regarding a fulfillment of the user's emotional goal.

11. The non-transitory computer readable medium of claim 10, wherein the user-perceptible output and elements in the set of user interface elements are reflective of a theme consistent with the at least one root emotion, such that the user-perceptible output and the set of user interface elements are each consistent with the root emotion by color, hue, or a combination thereof.

12. The non-transitory computer readable medium of claim 11, wherein the user-perceptible output comprises images or sounds that are semantically, tonally, thematically, or chromatically related to the at least one root emotion, wherein the main reason provides more specific details regarding the emotional intent of the user provided by the root emotion, and wherein the sub reason supports the main reason by specifying a conceptually narrower articulation of the emotional intent of the user.

13. The non-transitory computer readable medium of claim 11, wherein the user interface elements that prompt the user for more information specifying the emotional intent comprise images and sounds that are respectively semantically, tonally, thematically, and chromatically related to the at least one root emotion.

14. The non-transitory computer readable medium of claim 10, wherein each of a subsequent user interface element and a subsequent output are respectively dependent on a preceding user interface element interaction, and wherein a subsequent user-input is of a different type than a preceding user-input, wherein at least one user-input is a free-form fillable field input.

15. The non-transitory computer readable medium of claim 10, wherein the elements of the set of user interface elements are presented to a user in a sequence wherein each subsequent user interface element includes a prompt or a query eliciting a more precise description of the user's emotional goal than that provided by the user in response to a previous prompt or query presented to the user earlier in the sequence.

16. The non-transitory computer readable medium of claim 10, wherein a length of the iterative process depends on the desired level of precision and on a number of iterations of sequential affirmations and prompts presented to the user.

17. A system for ascertaining an emotional goal, comprising:
- at least one computing device having at least one processor device and at least one user interface having an input device and output device communicatively connected to the processor to:
  - receive a first user-input, via the at least one user interface, that is indicative of a purpose of a user's interaction with the at least one user interface, and to receive a second user-input indicative of a target person to whom the purpose of the user's interaction pertains after receiving the first user-input;
  - generate, by the at least one processor device, a prompt, based on both of the first user-input and the second user-input, for the user to provide at least one root reason for the interaction;
  - generate, by the at least one processor device, a visual, an audio, or an audio-visual output and a set of user interface elements dependent on the at least one root reason and presents the output and the set of user interface elements to the user via the output device;
  - present a sequence of user interface elements that are associated with the root reason and with the second user-input, after generating the set of user interface elements dependent on the at least one root reason;
  - prompt a user, via a first user element of the sequence, to indicate a main reason in support of the at least one root reason;
  - prompt the user, via a second user element of the sequence, to provide a sub reason in support of the main reason;
  - receive, a series of user-inputs wherein relative to a preceding user-input in the series, a subsequent user-input in the series further specifies an emotional intent that is conceptually narrower relative to the root reason of the user, wherein the emotional intent is defined relative to how the target person is desired to feel;
  - repeat an iterative process of affirming a previous user-input and prompting the user to provide more details specifying the emotional intent until a desired level of precision in determining the user's emotional goal is reached, wherein the desired level of precision is determined by a chosen number of times to repeat the iterative process; and
  - responsive to the desired level of precision being reached, determine, the user's emotional goal with respect to the target person based on the second user-input, on the at least one root reason, and on user-inputs provided via the sequence of user interface elements, to provide the user, via the output device, a recommendation regarding a fulfillment of the user's emotional goal.

18. The system of claim 17, wherein both the user-perceptible output and elements in the set of user interface elements that prompt the user for more information specifying the emotional intent are reflective of a theme consistent with the at least one root reason, such that the user-perceptible output and the set of user interface elements are consistent with the root reason by color, hue, or a combination thereof.

19. The system of claim 17, wherein each of a subsequent user interface element and a subsequent output are respectively dependent on a preceding user interface element interaction, and wherein a subsequent user-input is of a different type than a preceding user-input, wherein at least one user-input is a free-form Tillable field input.

20. The system of claim 17, wherein the elements of the set of user interface elements are presented to a user in a sequence wherein each subsequent user interface element includes a prompt or query eliciting a more precise description of the user's emotional goal than that provided by the user in response to a previous prompt or query presented to the user earlier in the sequence and wherein a length of the iterative process depends on the desired level of precision and on a number of iterations of sequential affirmations and prompts presented to the user.

* * * * *